United States Patent [19]

Fujita et al.

[11] Patent Number: 5,068,247

[45] Date of Patent: Nov. 26, 1991

[54] 2-AMINOPENTANOIC ACID COMPOUNDS AND THEIR USE AS IMMUNOSUPPRESSANTS

[75] Inventors: Tetsuro Fujita, Muko; Takeshi Ikumoto; Shigeo Sasaki, both of Kobe; Chiba Kenji; Yukio Hoshino, both of Tokyo, all of Japan

[73] Assignees: Yoshitomi Pharmaceutical Industries, Ltd., Osaka; Taito Co., Ltd., Tokyo, both of Japan

[21] Appl. No.: 549,137

[22] Filed: Jul. 5, 1990

[30] Foreign Application Priority Data

Jul. 7, 1989 [JP] Japan ................................. 1-176914

[51] Int. Cl.$^5$ ............................................. A61K 31/385
[52] U.S. Cl. ..................................... 514/440; 514/561; 514/564; 549/77; 562/560; 562/567; 562/564
[58] Field of Search .................. 502/567, 560, 564; 549/77; 514/440, 501, 564

[56] References Cited

U.S. PATENT DOCUMENTS 3,758,529  9/1973  Craveri ................................. 562/5
3,928,572  12/1975  Kluepfel et al. .................... 562/567

FOREIGN PATENT DOCUMENTS

90/02727  3/1990  World Int. Prop. O. .......... 562/507

OTHER PUBLICATIONS

Bagli et al., "J. Org. Chem.", 38(7) 1253–1260(1973).
"Chem. Abst.", 112(3):19950n (Jan. 15, 1990).

*Primary Examiner*—James H. Reamer
*Attorney, Agent, or Firm*—Wenderoth, Lind & Ponack

[57] ABSTRACT

There are disclosed 2-aminopentanoic acid compounds represented by the formula

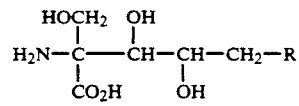

wherein R is as defined in the specification, their optical isomers, their pharmacologically acceptable salts and their use as an immunosuppressant.

4 Claims, No Drawings

2-AMINOPENTANOIC ACID COMPOUNDS AND THEIR USE AS IMMUNOSUPPRESSANTS

BACKGROUND OF THE INVENTION

This invention relates to 2-aminopentanoic acid compounds which are useful as pharmaceuticals, specifically as an immunosuppressant.

Recently, cyclosporin has been used as an agent for suppressing rejection in organ transplantation. The so-called immunosuppresants including compounds under development have been expected to be also effective as a therapeutic medicament for articular rheumatism, etc. Said cyclosporin, however, has a drawback that it causes side effects such as renal disturbances.

Meanwhile, Japanese Patent Publication No. 104087/1989 discloses that immunosuppressive substance can be obtained from a liquid culture of *Isaria sinclairii*, and it has been confirmed that said substance is (2S,3R,4R)-(E)-2-amino-3,4-dihydroxy-2-hydroxymethyl-14-oxoeicosa-6-enoic acid of the formula

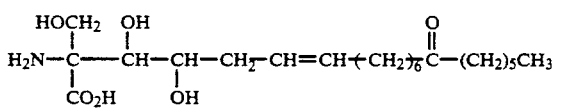

disclosed in U.S. Pat. No. 3,928,572.

SUMMARY OF THE INVENTION

The object of the invention is to provide novel 2-aminopentanoic acid compounds which exhibit excellent immunosuppressive action and less side effects.

DETAILED DESCRIPTION OF THE INVENTION

The present invention relates to 2-aminopentanoic acid compounds represented by the formula

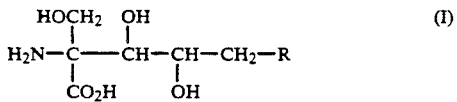

wherein R is an alkyl, a hydroxyalkyl or a group represented by the formula: $-CH=CH(CH_2)_nCH=CH-CH(OH)-(CH_2)_mCH_3$ wherein n and m stand for an integer of 1 to 10, respectively; $-CH=CH(CH_2)_pC(=X)-(CH_2)_qCH_3$ wherein $>C=X$ stands for

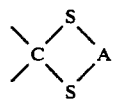

wherein A is an alkylene, $>C=N-OB$ wherein B is a hydrogen or an alkyl, or $>CHNH_2$ wherein p and q are respectively an integer of 1 to 10; or $-CH=CH-Y$ wherein Y is an alkyl, salts thereof, γ-lactone compounds thereof and compounds protected by their protective groups.

Referring to R in the present specification, mention is made of, for example, a straight- or a branched-alkyl having 1 to 30 carbon atoms such as methyl, ethyl, propyl, isopropyl, butyl, isobutyl, tert-butyl, pentyl, isopentyl, neopentyl, hexyl, octyl, 2-ethylhexyl, decyl, dodecyl, tetradecyl, hexadecyl, octadecyl, eicosyl and docosyl as the alkyl, and a hydroxyalkyl having 1 to 6 carbon atoms whose alkyl moiety may be branched, such as hydroxymethyl, 2-hydroxyethyl, 3-hydroxypropyl, 1-hydroxymethylethyl, 4-hydroxybutyl and 6-hydroxyhexyl as the hydroxyalkyl.

Referring to the substituent $=X$ in the present specification, mention may be made of, for example, an alkylene having 1 to 4 carbon atoms such as methylene, ethylene, trimethylene, propyridene and tetramethylene as the alkylene represented by A, and a straight- or a branched-alkyl having 1 to 4 carbon atoms such as methyl, ethyl, propyl, isopropyl, butyl and tert-butyl as the alkyl represented by B.

Referring to Y in the present specification, the alkyl is as defined above for R.

The γ-lactone compounds of the formula (I) are the compouds represented by the formula

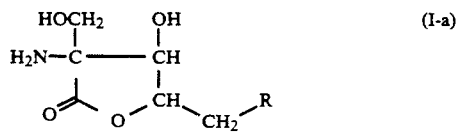

wherein R is as defined above.

The protective groups for the compounds of the formula (I) which have been protected by the protective groups are those widely used in organic chemistry for hydroxy group or an amino group, and examples thereof include acyl (e.g. acetyl, benzoyl), oxycarbonyl (e.g. tert-butoxycarbonyl) and tetrahydropyranyl.

Examples of salts of the compounds of the formula (I) include pharmaceutically acceptable salts such as metal salts (e.g. sodium salt, potassium salt, calcium salt, zinc salt, aluminium salt), salts with amines (e.g. triethylamine) and salts with amino acids (e.g. lysine, ornithine). Furthermore, hydrates, solvates, respective optical isomers, diastereoisomers and racemates are also encompassed in the present invention.

Preferred compounds (I) are as shown below:

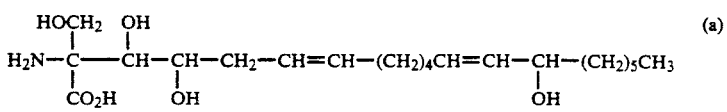

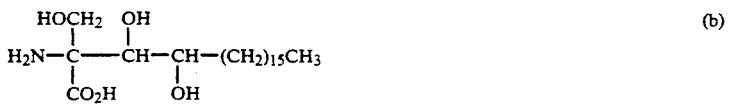

-continued

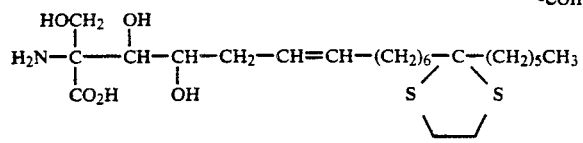  (c)

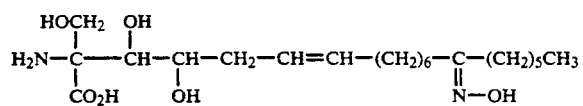  (d)

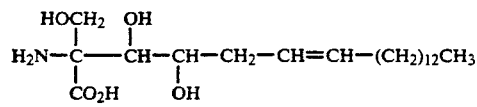  (e)

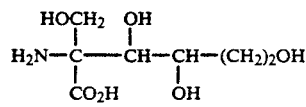  (f)

The compounds of the formula (I) can be prepared by using (2S,3R,4R)-(E)-2-amino-3,4-dihydroxy-2-hydroxymethyl-14-oxoeicosa-6-enoic acid (hereinafter referred to as ISP-I) obtained by fermentation method, etc. For example, Compound (a) can be produced by fermentation method, and as the microorganisms productive of Compound (a), mention is made of, for example, those belonging to Ascomycotina and Deuteromycotina, more specifically, genus Isaria and genus Mycelia belonging to Deuteromycotina and genus Myriococcum (Thielavia) belonging to Ascomycotina, which are respectively deposited at American Type Culture Collection as *Isaria sinclairii* ATCC No. 24400, *Myriococcum albomyces* ATCC No. 16425 and *Mycelia sterilia* ATCC No. 20349. The *Myriococcum albomyces* ATCC No. 16425 is deposited at Institute of Fermentatioon Organization, Osaka, Japan as IFO 32292.

Compound (a) can also be produced by a mutant which can be obtained by modification of a strain mentioned above by way of a conventional artificial mutating means such as ultraviolet rays, high-frequency radioactive rays and chemicals.

Compound (a)-producing microorganisms can be cultivated in various culture-media comprising usual nutrient sources for fungi. For example, there can be suitably added glucose, starch, glycerine, sugar millet jelly, dextrin, molasses, maltose, xylose, and the like as carbon sources; inorganic or organic nitrogen compounds such as corn steep liquor, peptone, yeast extract, potato extract, meat juice, soy bean meal, wheat germ, potassium nitrate, sodium nitrate, ammonium sulfate, casein, gluten meal, cotton seed meal, feather meal as nitrogen sources; other conventional inorganic salts; and conventional additives for cultivation, such as organic acid inorganic substances and antifoaming agents which help growth of microorganisms and promote production of Compound (a).

Though there is no particular limitation to the cultivation method thereof, aerobic submerged cultivation is more advantageous. The preferable culture temperature in the case of strains belonging to genus Isaria is in the range from 20° C. to 35° C., more preferably 25° to 30° C., and that in the case of the strains of genus Myriococcum or Mycelia is in the range from 30° C. to 50° C., preferably 35° C. to 45° C.

Compound (a) produced in the culture can be harvested from the culture by conventional procedures such as extraction, adsorption or by combination of conventional procedures. For example, in the case of strains as *Isaria sinclairii* belonging to genus Isaria, insoluble matters such as cells are removed by a separation method such as filtration or centrifugation, and the resulting culture filtrate is put in contact with Amberlite XAD-2 to adsorb Compound (a) for harvesting. The thus-obtained Compound (a) is eluted with in methanol, and subjected to reverse phase chromatography for fractionation to obtain highly purified Compound (a). In the case of strains such as *Myriococcum albomyces* and *Mycelia sterilia* which belong to genus Myriococcum or genus Mycelia, cells are removed from the culture solution by a separation method such as filtration or centrifugation, and the culture filtrate is subjected to the same procedure as that in the case of strains of genus Isaria. Meanwhile, Compound (a) is extracted from the separated cells with methanol and the extract is subjected to Amberlite XAD-2 as is the filtrate, followed by further purification such as chromatography or recrystallization to give Compound (a).

Compound (b) can be produced by reacting a γ-lactone compound derived from ISP-I (protected by a protective group), for example, a compound of the formula

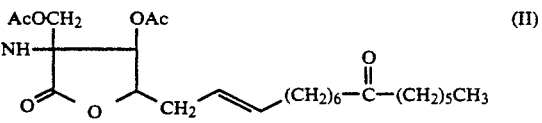  (II)

wherein Ac means an acetyl group with alkanedithiol in the presence of boron trifluoride to obtain the compound of the formula

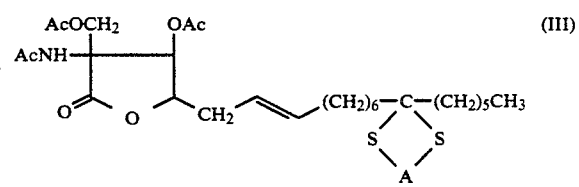  (III)

wherein Ac is as defined above and A is an alkylene, followed by reduction with Raney nickel, palladium carbon, etc. to yield the compound of the formula

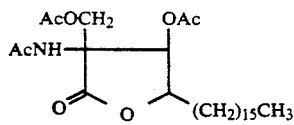

(IV)

wherein Ac is as defined above and alkali hydrolysis for breaking the lactone ring.

Compound (c) can be prepared by subjecting the compound of the formula (III) wherein A is ethylene to alkali hydrolysis reaction and Compound (d) can be prepared by reacting ISP-I with hydroxylamine. The alkoxime compound corresponding to Compound (d) can be obtained by reacting ISP-I with O-alkylhydroxylamine or reacting the hydroxime compound with dialkyl sulfate, alkyl iodide, etc. The thus-obtained hydroxime compound can be converted to an amine compound by a conventional method. Compound (d) or the corresponding alkoxime compound has geometric isomers such as anti- or syn-, and the present invention encompasses these isomers and the mixtures thereof.

Compound (e) can be produced by reducing the 14-position of the compound (II) to hydroxy with a metal hydrogen complex compound such as sodium borohydride or lithium aluminum hydride to convert into an alcohol compound, and reacting the obtained alcohol compound with 1,1'-thiocarbonyldiimidazole to substitute the 14-position thereof to 1-imidazorylthiocarbonyloxy, followed by radical reduction with, for example, tributyltin hydride to eliminate said substituent group and alkalin hydrolysis reaction. Another method wherein secondary hydroxyl group is trifluoromethanesulphonated, followed by deoxydization reaction with sodium borohydride can be employed.

Further, Compound (e) and be produced by, for example, subjecting the compound of formula (II) to Clemmensen reduction followed by breaking of the γ-lactone ring and deacethylation reaction.

The Clemmensen reduction is known per se, and the reaction of γ-lactone compound of the formula (II) wherein nitrogen and oxygen atoms are protected with zinc powder or zinc amalgam and hydrochloric acid in an inert solvent (e.g. benzene, toluene, xylene, methanol, ethanol, etc.) produces the compound wherein carbonyl group is reduced to methylene group. It is preferable to use anhydrous acetic acid saturated with hydrogen chloride in place of hydrochloric acid. The reaction proceeds at a room temperature or under heating for about 5 to 30 hours.

As the γ-lactone ring-breaking reaction and deacetylation reaction, mention can be made of alkali hydrolysis reaction.

Compound (f) can be produced by subjecting a γ-lactone compound of ISP-I, namely, compound (II) to ozonolysis reaction or 1,2-diol-forming reaction with osmium oxide, followed by reaction with sodium periodate and reduction with sodium borohydride.

The compound of the formula (I) wherein R is —CH=CH—Y can be produced by subjecting ISP-I to ozonolysis reaction, followed by reaction with Witting reagent.

The thus-obtained compound can be converted to the corresponding γ-lactone compound by treatment with an acid such as hydrochloric acid and acetic acid or tertiary alcohol such as tertiary pentyl alcohol.

The afore-mentioned reaction proceeds without any solvent or in an inert solvent under cooling, at room temperature or under heating for about 5 minutes to 50 hours.

The compounds of the formula (I) of the present invention, namely, carboxylic acid compounds can be converted to the above-mentioned salts by conventional methods. Further, various isomers can be produced by optical resolution of racemic compounds and diastereoisomers or employing an optically active starting material.

The 2-aminopentanoic acid compounds of the present invention possess excellent immunosuppressive actions, and therefore are usable as a suppressive agent for rejection in organ or marrow transplantation, as a prophylactic or therapeutic agent for autoimmune diseases such as rheumatoid arthritis, systemic lupus erythematosus, Sjogren's syndrome, multiple sclerosis, grave myasthenia, I-type diabetes, endocrine ophthalmopathy, primary biliary cirrhosis, Crohn's diseases, glomerulonephritis, sarcoidosis, psoriasis, pemphigus, hypoplastic anemia, idiopathic thrombocytopenic purpura and allergy, or as a medical and pharmaceutical reagent to mammals such as humans, cattles, horses, dogs, mice, rats and so on.

These compounds are admixed with carriers, excipients, diluents and the like to be formulated into dosage forms such as powders, capsules, tablets, injections for administration to patients. They may also be lyophilized into a pharmaceutical composition by a per se known means.

While the dosage of these compounds varies depending on diseases, symptoms, body weight, sex, age and so on, for the suppression in kidney transplantation, for example, they can be usually administered at the daily dosage per adult of 0.1–10 mg (potency), in one to several divided doses.

The following examples will illustrate the action and effects of this invention in more detail. Immunosuppressive activities were assayed by the following methods.

Said activities are assyed based on various immune reactions using mouse, rat and human lymphocytes; for example, immunosuppressive activities are assayed with high sensitivity by using mouse, rat or human allogenic mixed lymphocyte reactions (allogenic MLR). Allogenic MLR is blastogenesis of lymphocytes induced by mixed culture of lymphocytes derived from two individuals that are allogenic but different in their major histocompatibility antigens, such as spleen cells, lymph node cells and peripheral blood lymphocytes. This allogenic MLR is a reaction representing a phenomenon which reflects the difference in the major histocompatibility antigens among the donors; for example, blastogenesis of lymphocytes cannot be observed by the mixed culture of lymphocytes from monozygotic twins. Therefore, allogenic MLR is widely used for selection of the donor and the recipient in organ transplantation.

It is usual for allogenic MLR that the lymphocytes from one of the two donors are used as stimulator cells after treatment with X-ray irradiation or with mitomycin C to inhibit their mitotic proliferation, while blastogenesis of the lymphocytes from the other donor (responder cells) is measured (one way-MLR).

Immunosuppressive activities can be determined also by measuring the activities to suppress the induction of major histocompatibility antigens-restricted cytotoxic T cells in allogenic MLR.

In addition, immunosuppressive activities can be evaluated also as the activities to suppress blastogenesis of lymphocytes induced by stimulation with various mitogens (e.g. concanavalin A, phytohemagglutinin, pokeweed mitogen, etc.), or as the activities to suppress the mitotic proliferation or expression of functions of lymphocytes induced by cytokines (e.g. interleukin 1, 2, 3, 4, 5, 6, etc.) which enhance the mitotic proliferation or promote differentiation of lymphocytes such as T cells and B cells. Immunosuppressive activities can also be evaluated as the activities to suppress the production of such cytokines from T cells, macrophages, etc.

Immunosuppressive activities can also be evaluated as the activities to suppress the induction of allogenic cells-specific cytotoxic T cells induced within mouse spleen cells which have been immunized in advance with allogenic cells, etc. and to suppress the production of the allogenic cells-specific antibodies produced in mouse serum immunized with allogenic cells, etc. or as the activities to suppress rejection in organ transplantation from allogenic mice, graft-versus-host reaction, delayed type allergy, adjuvant arthritis, etc. by intraperitoneal, oral, intraveous or intradermal administration of the compounds to mice.

Furthermore, immunosuppressive activities can be evaluated as the suppression of production of anti-DNA antibody, production of rheumatoid factor, nephritis, abnormal proliferation of lymphocytes, production of urine protein, or as the life-prolonging effect in MRL/lpr mice, NZB/WF$_1$ mice, BXSB mice or NOD mice, which are the model mice of autoimmune diseases, by the administration of the compounds.

EXPERIMENT EXAMPLE 1

Immunosuppressive Activity of Immunosuppressive Compounds

The immunosuppressive activity of the compounds was assayed on the basis of mouse allogenic mixed lymphocyte reaction (hereinafter sometimes abbreviated as MLR). Mouse allogenic MRL was carried out using a mixed culture of BALB/c mouse (H-$2^d$) spleen cells as the responder cells and mitomycin C-treated C57BL/6 (H-$2^6$) mouse spleen cells as the stimulator cells in equal amounts.

The responder cells were prepared as follows:

The spleen was resected from 5- to 6-week-old BALB/c mice, and single cell suspension of spleen cells was prepared by using the RPMI1640 culture medium (containing 60 μg/ml of kanamycin sulfate, 2 mM of L-glutamine, 10 mM of N-2-hydroxyethylpiperazine-N'-2-ethanesulphonate (HEPES) and 0.1% sodium hydrogencarbonate) to which heat-inactivated fetal calf serum (hereinafter sometimes abbreviated as FCS) had been added to 5%. After hemolytic treatment, the cell suspension was adjusted to a concentration of $10^7$ cells/ml with the RPMI1640 culture medium supplemented with $10^{-4}$M 2-mercapto-ethanol and 20% FCS, and was used as the responder cell suspension.

The stimulator cells were prepared as follows: The spleen was resected from 5- to 6-week-old male C57BL/6 mice, and a single cell suspension of spleen cells was prepared by using the RPMI1640 culture medium. After hemolytic treatment, the cells were treated with 40 μg/ml of mitomycin C at 37° C. for 60 minutes. After washing three times, the cell suspension was adjusted to a concentration of $10^7$ cells/ml with the RPMI1640 culture medium supplemented with $10^{-4}$M 2-mercapto-ethanol and 20% FCS, and was used as the stimulator cell suspension.

Fifty μl of the responder cell suspension, 50 μl of the stimulator cell suspension prepared by the above method, and 100 μl of the test substance were placed in a 96-well flat-bottomed microtest plate, and cultured at 37° C. in an atmosphere of 5% carbon dioxide and 95% air for 4 days.

The blastogenesis of lymphocytes was assayed using $^3$H-thymidine uptake as an index. That is, after termination of culture, 18.5 KBq/well of $^3$H-thymidine was added thereto and the suspension was cultured for 4 hours. Cells were harvested by a cell-harvester, and the radioactivity incorporated into the cells was determined by a liquid scintillation counter, which was used as an index of blastogenesis of lymphocytes in the mouse allogenic MLR. The suppression of the mouse allogenic MLR was evaluated by calculating the percent suppression by the following formula. The results are summarized in Table 1A.

TABLE 1A

| Responder cell | Stimulator cell | Test substance | Dose (μg/ml) | $^3$H-thymidine uptake (cpm) | Suppression (%) |
|---|---|---|---|---|---|
| BALB/c | — | — | — | 1628 | — |
| — | C57BL/6 | — | — | 226 | — |
| BALB/c | C57BL/6 | — | — | 18434 | — |
| BALB c | C57BL/6 | compound of Example 1 | 0.0001 | 17985 | 2.7 |
| | | | 0.001 | 13566 | 29.0 |
| | | | 0.01 | 11016 | 44.1 |
| | | | 0.1 | 1020 | 100.0 |
| | | | 1 | 919 | 100.0 |
| | | compound of Example 2 | 0.001 | 17981 | 2.7 |
| | | | 0.01 | 12011 | 38.2 |
| | | | 0.1 | 2329 | 95.8 |
| | | | 1 | 1869 | 98.6 |
| | | compound of Example 3 | 0.0001 | 17247 | 7.1 |
| | | | 0.001 | 16263 | 12.9 |
| | | | 0.01 | 13978 | 26.5 |
| | | | 0.1 | 14747 | 21.9 |
| | | | 1 | 631 | 96.2 |
| | | compound of Example 4 | 0.0001 | 16905 | 9.1 |
| | | | 0.001 | 15970 | 14.7 |
| | | | 0.01 | 15399 | 18.1 |
| | | | 0.1 | 1637 | 99.9 |
| | | | 1 | 1477 | 100.0 |
| | | compound of Example 5 | 0.0001 | 15747 | 16.0 |
| | | | 0.001 | 2384 | 95.5 |
| | | | 0.01 | 1421 | 100.0 |
| | | | 0.1 | 1091 | 100.0 |

TABLE 1A-continued

| Responder cell | Stimulator cell | Test substance | Dose ($\mu$g/ml) | $^3$H-thymidine uptake (cpm) | Suppression (%) |
|---|---|---|---|---|---|
| | | | 1 | 1163 | 100.0 |
| | | compound of Example 6 | 0.0001 | 16771 | 9.9 |
| | | | 0.001 | 13692 | 18.5 |
| | | | 0.01 | 13806 | 27.5 |
| | | | 0.1 | 14508 | 23.4 |
| | | | 1 | 7545 | 64.8 |

TABLE 1B

| Responder cell | Stimulator cell | Test substance | Dose ($\mu$g/ml) | $^3$H-thymidine uptake (cpm) | Suppression (%) |
|---|---|---|---|---|---|
| BALB/c | — | — | — | 645 ± 321 | — |
| — | C57BL/6 | — | — | 20 ± 13 | — |
| BALB/c | C57BL/6 | — | — | 5334 ± 1854 | — |
| | | compound of Example 5 | 0.0001 | 4485 ± 812 | 18.1 |
| | | | 0.001 | 6101 ± 356 | 0 |
| | | | 0.01 | 1013 ± 314 | 92.2 |
| | | | 0.1 | 359 ± 54 | 100.0 |
| | | | 1 | 52 ± 24 | 100.0 |
| | | potassium salt of compound of Example 5 | 0.0001 | 5622 ± 898 | 0 |
| | | | 0.001 | 4984 ± 3755 | 7.5 |
| | | | 0.01 | 1324 ± 16 | 85.5 |
| | | | 0.1 | 787 ± 257 | 97.0 |
| | | | 1 | 783 ± 28 | 97.1 |

$$\text{percent suppression (\%)} = \left(1 - \frac{\text{cpm in MLR with test substance} - \text{cpm in responder cells alone}}{\text{cpm in MLR without test substance} - \text{cpm in responder cells alone}}\right) \times 100$$

The test substance dissolved in methanol was diluted with the RPMI1640 culture medium and put to use. Methanol was used at a concentration of 0.01% or less, which concentration did not affect the allogenic MLR at all.

The compounds of Examples 1 to 6 in the final concentration range of 1 $\mu$g/ml to 0.0001 $\mu$g/ml were examined for their suppressive activity for blastogenic response of lymphocytes in mouse allogenic MLR. As shown in Table 1A, these compounds exhibited the suppressive activity in mouse allogenic MLR in a concentration-dependent manner.

It is found that the 50%-inhibition concentration (IC$_{50}$) of the compounds of Example 1 to Example 6 in mouse allogenic MLR are respectively 1.3×10$^{-2}$ $\mu$g/ml, 1.6×10$^{-2}$ $\mu$g/ml, 2.5×10$^{-1}$ $\mu$g/ml, 2.5×10$^{-2}$ $\mu$g/ml, 2.5×10$^{-4}$ $\mu$g/ml and 4.5×10$^{-2}$ $\mu$g/ml. As is evident from the results shown in Table 1B, the sodium salt of the compound of Example 5 showed almost the equivalent suppressive activity in mouse allogenic MLR to that of the compound of Example 5.

Blastogenesis of lymphocytes can be evaluated also by the following colorimetry using 3-(4,5-dimethylthiazol-2-yl)-2,5-diphenyltetrazolium bromide (MTT).

The supernatant (100 $\mu$l) is removed from each well after termination of culture, and 20 $\mu$l of a 5 mg/ml MTT solution is added to each well, which is cultured at 37° C. for 4 hours. Thereafter, 100 $\mu$l of a 0.01N hydrochloric acid solution containing 10% sodium dodecylsulfate is added thereto and cultured at 37° C. overnight to dissolve the resultant purple crystals of formazan. The absorbancy at 570 nm is measured using a microplate absorption spectro-photometer (immunoreader) as an index of blastogenic response of lymphocytes in mouse allogenic MLR. Suppression of mouse allogenic MLR is evaluated by calculating the percent suppression by the following formula:

$$\text{percent suppression (\%)} = \left(1 - \frac{\text{absorbancy in MLR with test substance} - \text{absorbancy in responder cells alone}}{\text{absorbancy in MLR without test substance} - \text{absorbancy in responder cells alone}}\right) \times 100$$

EXPERIMENT EXAMPLE 2

Human allogenic MLR-suppressive activity

The human allogenic MLR-suppressive activity was assayed as follows:

Human peripheral blood lymphocytes obtained by Ficoll-Paque density gradient centrifugation of normal human peripheral blood were suspended in the RPMI1640 culture medium supplemented with 10% FCS, placed in a plastic dish, and cultured in an atmosphere of 5% carbon dioxide and 95% air at 37° C. for 2 hours. After termination of culture, the supernatant after gentle pipetting was collected and centrifuged (1000 rpm, for 5 minutes) to obtain plastic-nonadherent cells. The plastic-nonadherent cells were allowed to pass through a nylon-wool column to give nylon-nonadherent cells, and the concentration of the cell suspension was adjusted to 4×10$^6$ cells/ml by using the RPMI1640 culture medium supplemented with 10% FCS, and used as the responder cell suspension.

The plastic-adherent cells were removed from the plastic dish by vigorous pipetting after addition of phosphate buffered saline (PBS) supplemented with 5% FCS and 0.02% disodium ethylenediaminetetraacetic acid (EDTA). The plastic-adherent cells were treated with 40 $\mu$g/ml of mitomycin C at 37° C. for 60 minutes, washed three times, and suspended to the concentration of 4×10$^6$ cells/ml in the RPMI1640 culture medium supplemented with 10% FCS. The resultant suspension was used as the stimulator cell suspension. Fifty $\mu$l of the responder cell suspension from the donor A or C was mixed with 50 μl of the stimulator cell suspension from the donor B or D, to which 100 μl of the test substance was added, and cultured at 37° C. in an atmosphere of 5% carbon dioxide and 95% air for 5 days.

After termination of culture, 37 KBq/well of ³H-thymidine was added, and after 18 hours of culture, the cells were harvested by a cell-harvester. The radioactivity incorporated into the cells was measured by a liquid scintillation counter, which was used as an index of blastogenic response of lymphocytes in human allogenic MLR. The suppression of human allogenic MLR was evaluated by calculating the percent suppression by the following formula. The results are summarized in Table 2A and Table 2B.

$$\text{percent suppression (\%)} = \left(1 - \frac{cpm, \text{ in } MLR \text{ with test substance} - cpm, \text{ in responder cells alone}}{cpm, \text{ in } MLR \text{ without test substance} - cpm, \text{ in responder cells alone}}\right) \times 100$$

TABLE 2A

| Responder cell | Stimulator cell | Test substance | Dose (μg/ml) | ³H-thymidine uptake (cpm) | Suppression (%) |
|---|---|---|---|---|---|
| Donor A | — | — | — | 738 | — |
| — | Donor B | — | — | 79 | — |
| Donor A | Donor B | — | — | 11895 | — |
| Donor A | Donor B | compound of Example 1 | 0.001 | 12137 | 0 |
| | | | 0.01 | 7479 | 39.6 |
| | | | 0.1 | 5590 | 56.5 |
| | | | 1 | 5613 | 56.3 |
| | | compound of Example 2 | 0.001 | 9258 | 23.6 |
| | | | 0.01 | 8119 | 33.8 |
| | | | 0.1 | 4624 | 65.2 |
| | | | 1 | 7130 | 42.7 |
| | | compound of Example 3 | 0.0001 | 10700 | 10.7 |
| | | | 0.001 | 7285 | 41.3 |
| | | | 0.01 | 7790 | 36.8 |
| | | | 0.1 | 6582 | 47.6 |
| | | | 1 | 5909 | 53.7 |
| | | compound of Example 5 | 0.00001 | 14723 | 0 |
| | | | 0.0001 | 8052 | 34.4 |
| | | | 0.001 | 5363 | 58.5 |
| | | | 0.01 | 5042 | 61.4 |
| | | | 0.1 | 4660 | 64.8 |
| | | | 1 | 5545 | 56.9 |

TABLE 2B

| Responder cell | Stimulator cell | Test substance | Dose (μg/ml) | ³H-thymidine uptake (cpm) | Suppression (%) |
|---|---|---|---|---|---|
| Donor C | — | — | — | 440 | — |
| — | Donor D | — | — | 771 | — |
| Donor C | Donor D | — | — | 20065 | — |
| Donor C | Donor D | compound of Example 1 | 0.0001 | 20334 | 1.4 |
| | | | 0.001 | 15284 | 24.4 |
| | | | 0.01 | 7232 | 65.4 |
| | | | 0.1 | 5292 | 75.3 |
| | | | 1 | 6689 | 68.2 |
| | | compound of Example 2 | 0.00001 | 13909 | 31.4 |
| | | | 0.0001 | 15259 | 24.5 |
| | | | 0.001 | 15503 | 23.2 |
| | | | 0.01 | 11263 | 44.9 |
| | | | 0.1 | 7300 | 65.0 |
| | | | 1 | 6583 | 68.7 |
| | | compound of Example 3 | 0.0001 | 18512 | 7.9 |
| | | | 0.001 | 17138 | 14.9 |
| | | | 0.01 | 15337 | 24.1 |
| | | | 0.1 | 8187 | 60.5 |
| | | | 1 | 5143 | 76.0 |
| | | compound of Example 5 | 0.0001 | 15723 | 22.1 |
| | | | 0.001 | 7145 | 65.8 |
| | | | 0.01 | 5878 | 72.3 |
| | | | 0.1 | 4703 | 78.3 |
| | | | 1 | 5601 | 73.7 |

The compounds of Examples 1, 2, 3 and 5 in the final concentration range of 1 μg/ml to 0.0001 μg/ml were examined for their suppressive activity on blastogenic response of lymphocytes in human allogenic MLR. As shown in Table 2A and Table 2B, these compounds exhibited suppressive activity in human allogenic MLR in a concentration-dependent manner.

EXPERIMENT EXAMPLE 3

Suppression of induction of allo-reactive cytotoxic T cell in mouse allogenic mixed lymphocyte culture (MLC)

The spleen cell suspension, 0.5 ml, ($2 \times 10^7$ cells/ml) of BALB/c mouse (H-$2^d$), 0.5 ml of a suspension of mitomycin C-treated C57BL/6 mouse (H-$2^b$) spleen cells ($2 \times 10^7$ cells/ml) and 1.0 ml of the test substance, which had been prepared in the same manner as in Experiment Example 1, were added to a 24-well multidish, and cultured at 37° C. in an atmosphere of 5% carbon dioxide and 95% air for 6 days.

After termination of culture, the cells were harvested by centrifugation, and the concentration of the cell suspension was adjusted to $5 \times 10^6$–$6.25 \times 10^5$ cell/ml by using the RPMI1640 culture medium supplemented with 10% FCS, and used as the effector cell suspension.

The target cells used were leukemia cells EL4 from the syngenic (H-$2^b$) C57BL/6 mouse as used for preparation of the stimulator cells. By incubating $10^6$ EL4 cells in the presence of 370 KBq of Na$_2$$^{51}$CrO$_4$ at 37° C. for 1 hour, $^{51}$Cr was incorporated into the cytoplasm. The cells were washed, adjusted to the concentration of $10^4$ cells/ml and used as the target cells.

For the assay of the cytotoxic activity, 100 μl of the effector cell suspension and 100 μl of the target cell suspension were added to a 96-well flat-bottomed microculture plate, and cultured at 37° C. for 4 hours. The amount of $^{51}$Cr released into the supernatant was determined and the cytotoxic activity was calculated by the following formula. The results are summarized in Table 3A.

$$\text{cytotoxic activity (\%)} = \left(1 - \frac{\text{cpm, effector cells} + \text{target cells} - \text{cpm, target cells alone}}{\text{cpm, target cells treated with 0.1 N HCl} - \text{cpm, target cells alone}}\right) \times 100$$

TABLE 3A

| Effector cells | | Target cell | Test substance | Dose (μg/ml) | Cytotoxic activity (LU/$10^6$) | Suppression (%) |
| responder cell | stimulator cell | | | | | |
| --- | --- | --- | --- | --- | --- | --- |
| BALB/c | — | EL4 | — | — | <1.0 | — |
| BALB/c | C57BL/6 | EL4 | — | — | 19.6 | — |
| BALB/c | C57BL/6 | EL4 | compound of Example 2 | 0.001 | 16.0 | 18.4 |
| BALB/c | C57BL/6 | EL4 | | 0.01 | 13.0 | 33.6 |
| BALB/c | C57BL/6 | EL4 | | 0.1 | <1.0 | >95 |
| BALB/c | C57BL/6 | EL4 | | 1 | <1.0 | >95 |
| BALB/c | — | EL4 | — | — | <0.5 | — |
| BALB/c | C57BL/6 | EL4 | — | — | 13.9 | — |
| BALB/c | C57BL/6 | EL4 | compound of Example 5 | 0.0001 | 9.2 | 34.1 |
| BALB/c | C57BL/6 | EL4 | | 0.001 | 3.7 | 73.2 |
| BALB/c | C57BL/6 | EL4 | | 0.01 | 1.6 | 88.4 |
| BALB/c | C57BL/6 | EL4 | | 0.1 | <0.5 | >95 |
| BALB/c | C57BL/6 | EL4 | | 1 | <0.5 | >95 |

TABLE 3B

| Effector cells | | Target cell | Test substance | Dose (μg/ml) | Cytotoxic activity (LU/$10^6$) | Suppression (%) |
| responder cell | stimulator cell | | | | | |
| --- | --- | --- | --- | --- | --- | --- |
| C3H/HeN | — | EL4 | — | — | <0.5 | — |
| C3H/HeN | C57BL/6 | EL4 | — | — | 15.2 | — |
| C3H/HeN | C57BL/6 | EL4 | compound of Example 5 | 0.00001 | 9.8 | 35.4 |
| C3H/HeN | C57BL/6 | EL4 | | 0.0001 | 8.0 | 47.5 |
| C3H/HeN | C57BL/6 | EL4 | | 0.001 | 6.8 | 54.2 |
| C3H/HeN | C57BL/6 | EL4 | | 0.01 | <0.5 | >95 |
| C3H/HeN | C57BL/6 | EL4 | | 0.1 | <0.5 | >95 |
| C3H/HeN | C57BL/6 | EL4 | | 1 | <0.5 | >95 |

The cytotoxic T cells induced by the method described above exhibited a strong cytotoxic activity to the EL4 cells (H-$2^b$) which are syngenic with the stimulator cells (H-$2^b$), whereas they were not cytotoxic to the allogenic Meth A cells (H-$2^d$), P815 cells (H-$2^d$) and BW5147 cells (H-$2^k$), and thus it was indicated that they were H-$2^b$-restricted allo-reactive cytotoxic T cells. The activity of the cytotoxic T cell is expressed by LU (lytic unit) per $10^6$ effector cells. One lytic unit (LU) is defined as the number of effector cells required to cause 25% lysis of $5 \times 10^3$ target cells.

As shown in Table 3A, addition of the compound of Example 2 or 5 markedly inhibited the induction of the allo-reactive cytotoxic T cell.

When a suspension of C3H/HeN mouse (H-$2^k$) spleen cells was used as the responder cell suspension and the suspension of mitomycin C-treated C57BL/6 mouse (H-$2^b$) spleen cells was used as the stimulator cell suspension, the induction of the allo-reactive cytotoxic T cell was suppressed also by addition of the compound of Example 5 (Table 3B).

EXPERIMENT EXAMPLE 4

Suppression of interleukin 2 (IL-2) and IL-3 production in mitogen-stimulated mouse spleen cells The suppression of IL-2 and IL-3 production in the mitogen-stimulated mouse spleen cells was examined as follows:

The spleen was resected from 5- to 8-week-old male C3H/HeN mice, and a single cell suspension of spleen cells was prepared by using the RPMI1640 culture medium. After hemolytic treatment, the concentration of the suspension was adjusted to $10^7$ cells/ml by using the RPMI1640 culture medium supplemented with 20% FCS, to which 10 μg/ml of phytohemagglutinin (PHA) was added as mitogen. One ml of the cell suspension and 1 ml of the test substance were added to a 24-well multidish, and cultured at 37° C. in an atmosphere of 5% carbon dioxide and 95% air for 24 hours. After termination of culture, the supernatant was collected and used as the culture supernatant of PHA-stimulated mouse spleen cells.

The IL-2 activity in the culture supernatant of PHA-stimulated mouse spleen cells was assayed as follows:

IL-2 dependent mouse cell line CTLL-2 cells were suspended in the RPMI1640 culture medium supplemented with 30% FCS to the concentration of $2 \times 10^5$ cells/ml. One hundred μl of the cell suspension and 100 μl of the two-fold serial dilution of the culture supernatant of PHA-stimulated mouse spleen cells were added to a 96-well flat-bottomed microtest plate. After culturing at 37° C. in an atmosphere of 5% carbon dioxide and 95% air for 44 hours, the absorbancy was measured by the colorimetry using MTT, in the same way as in Experiment Example 1, which was used as an index of IL-2-dependent cell proliferation. The IL-2 activity is expressed in U/ml as the dilution at which the absorbancy measured by MTT method was 50% of the maximum.

The IL-3 activity was assayed as follows:

IL-3-dependent mouse cell line FDC-P2 cells were suspended in the RPMI1640 culture medium supplemented with 10% FCS to the concentration of $2 \times 10^5$ cells/ml. One hundred μl of the cell suspension and 100 μl of the two-fold serial dilution of the culture supernatant of PHA-stimulated mouse spleen cells described above were added to a 96-well flat-bottomed microtest plate. After culturing at 37° C. in an atmosphere of 5% carbon dioxide and 95% air for 44 hours, the absorbancy was measured by the colorimetry using MTT, in the same way as described above, which was used as an index of IL-3-dependent cell proliferation. The IL-3 activity is expressed in U/ml as the dilution at which the absorbancy measured by MTT method was 50% of the maximum.

TABLE 4A

| Sample | IL-2 activity (U/ml) | Suppression (%) |
| --- | --- | --- |
| Unstimulated culture supernatant | <1 | — |
| Culture supernatant stimulated with PHA | 12.1 | — |
| PHA-stimulated culture supernatant treated with compound of Example 1 | | |
| (0.001 μg/ml) | 13.9 | 0 |
| (0.01 μg/ml) | 6.1 | 49.6 |
| (0.1 μg/ml) | 3.7 | 69.4 |
| (1 μg/ml) | 2.0 | 83.5 |
| PHA-stimulated culture supernatant treated with compound of Example 2 | | |
| (0.001 μg/ml) | 12.1 | 0 |
| (0.01 μg/ml) | 7.0 | 42.1 |
| (0.1 μg/ml) | 6.1 | 49.6 |
| (1 μg/ml) | 3.7 | 69.4 |
| PHA-stimulated culture supernatant treated with compound of Example 3 | | |
| (0.001 μg/ml) | 14.9 | 0 |
| (0.01 μg/ml) | 13.9 | 0 |
| (0.1 μg ml) | 12.6 | 0 |
| (1 μg/ml) | 8.6 | 28.9 |
| Unstimulated culture supernatant | <1 | — |
| Culture supernatant stimulated with PHA | 13.5 | — |
| PHA-stimulated culture supernatant treated with compound of Example 5 | | |
| (0.001 μg/ml) | 8.6 | 36.3 |
| (0.01 μg/ml) | 4.6 | 65.9 |
| (0.1 μg/ml) | 4.3 | 68.1 |
| (1 μg/ml) | 2.7 | 80.0 |
| PHA-stimulated culture supernatant treated with compound of Example 6 | | |
| (0.001 μg/ml) | 12.6 | 6.7 |
| (0.01 μg/ml) | 10.2 | 24.4 |
| (0.1 μg/ml) | 9.5 | 29.6 |
| (1 μg/ml) | 8.3 | 38.5 |

TABLE 4B

| Sample | IL-3 activity (U/ml) | Suppression (%) |
| --- | --- | --- |
| Unstimulated culture supernatant | <2 | — |
| Culture supernatant stimulated with PHA | 36.8 | — |
| PHA-stimulated culture supernatant treated with compound of Example 1 | | |
| (0.001 μg/ml) | 34.3 | 6.8 |
| (0.01 μg/ml) | 27.9 | 24.2 |
| (0.1 μg/ml) | 12.2 | 66.8 |
| (1 μg/ml) | 10.5 | 71.5 |
| PHA-stimulated culture supernatant treated with compound of Example 2 | | |
| (0.001 μg/ml) | 26.0 | 29.3 |
| (0.01 μg/ml) | 13.9 | 62.2 |
| (0.1 μg/ml) | 11.3 | 69.3 |
| (1 μg/ml) | 7.5 | 79.6 |
| PHA-stimulated culture supernatant treated with compound of Example 3 | | |
| (0.001 μg/ml) | 42.2 | 0 |
| (0.01 μg/ml) | 45.3 | 0 |
| (0.1 μg/ml) | 42.2 | 0 |
| (1 μg/ml) | 27.9 | 24.2 |
| Unstimulated culture supernatant | <2 | — |
| Culture supernatant stimulated with PHA | 24.5 | — |
| PHA-stimulated culture supernatant treated with compound of Example 5 | | |
| (0.001 μg/ml) | 22.0 | 10.2 |
| (0.01 μg/ml) | 13.2 | 10.2 |
| (0.1 μg/ml) | 12.0 | 51.0 |
| (1 μg/ml) | 9.5 | 62.2 |
| PHA-stimulated culture supernatant treated with compound of Example 6 | | |
| (0.001 μg/ml) | 23.8 | 2.9 |
| (0.01 μg/ml) | 23.4 | 4.5 |
| (0.1 μg/ml) | 23.3 | 4.9 |
| (1 μg/ml) | 20.0 | 18.4 |

As shown in Tables 4A and 4B, it was indicated that the compounds of the present invention suppressed the IL-2 and IL-3 production in the PHA-stimulated mouse spleen cells.

EXPERIMENT EXAMPLE 5

Suppression of IL-2 and IL-3 Production in Mouse Allogenic Mixed Lymphocyte Culture (MLC)

Mouse allogenic MLC was carried out as follows:

The responder cell suspension and the stimulator cell suspension (0.5 ml each) prepared in the same way as in Experiment Example 1 were added to a 24-well multidish, to which 1 ml of the test substance had been placed, and cultured at 37° C. in an atmosphere of 5% carbon dioxide for 2 days. After termination of culture, the supernatant was collected and used as the supernatant of mouse allogenic MLC.

The IL-2 and IL-3 activities in the supernatant of mouse allogenic MLC were assayed in the same way as in Experiment Example 4.

TABLE 5A

| Sample | IL-2 activity (U/ml) | Suppression (%) |
|---|---|---|
| culture supernatant of responder cells alone | <1.0 | — |
| Culture supernatant of MLC | 4.5 | — |
| Supernatant of MLC treated with compound of Example 2 | | |
| (0.0001 µg/ml) | 3.9 | 13.3 |
| (0.001 µg/ml) | 3.1 | 31.1 |
| (0.01 µg/ml) | 3.6 | 17.8 |
| (0.1 µg/ml) | 1 | 68.9 |
| (1 µg/ml) | 1.6 | 64.4 |
| Supernatant of MLC treated with compound of Example 5 | | |
| (0.0001 µg/ml) | 3.2 | 28.9 |
| (0.001 µg/ml) | 2.9 | 35.6 |
| (0.01 µg/ml) | <1.0 | 100 |
| (0.1 µg/ml) | <1.0 | 100 |
| (1 µg/ml) | <1.0 | 100 |

TABLE 5B

| Sample | IL-3 activity (U/ml) | Suppression (%) |
|---|---|---|
| culture supernatant of responder cells alone | 10.0 | — |
| Culture supernatant of MLC | 49.2 | — |
| Supernatant of MLC treated with compound of Example 2 | | |
| (0.0001 µg/ml) | 42.8 | 16.3 |
| (0.001 µg/ml) | 45.3 | 9.9 |
| (0.01 µg/ml) | 42.2 | 17.9 |
| (0.1 µg/ml) | 23.6 | 65.3 |
| (1 µg/ml) | 11.0 | 97.4 |
| Supernatant of MLC treated with compound of Example 5 | | |
| (0.0001 µg/ml) | 32.7 | 42.1 |
| (0.001 µg/ml) | 19.2 | 76.5 |
| (0.01 µg/ml) | 11.5 | 96.2 |
| (0.1 µg/ml) | 7.9 | 100 |
| (1 µg/ml) | 7.9 | 100 |

As shown in Tables 5A and 5B, it was indicated that the compounds of the present invention suppressed the production of IL-2 and IL-3 in mouse allogenic MLC.

EXPERIMENT EXAMPLE 6

Suppression of Proliferation of IL-2-Dependent Mouse Cell Line CTLL-2 Induced by Interleukin 2 (IL-2)

IL-2-dependent mouse cell line CTLL-2 cells were suspended in the RPMI1640 culture medium supplemented with 30% FCS to the concentration of $4 \times 10^5$ cells/ml. Fifty µl of the cell suspension, 50 µl of 200 U/ml recombinant human IL-2 (rhIL-2) and 100 µl of the test substance were added to a 96-well flat-bottomed microtest plate. After culturing at 37° C. in an atmosphere of 5% carbon dioxide and 95% air for 68 hours, the absorbancy was measured by the colorimetry using MTT, in the same way as in Experiment Example 1, which was used as an index of proliferation of IL-2-dependent cells. The percent suppression (%) was calculated by the following formula.

$$\text{percent suppression} = \left(1 - \frac{\text{absorbancy with rhIL-2 and test substance} - \text{absorbancy without rhIL-2}}{\text{absorbancy with rhIL-2} - \text{absorbancy without rhIL-2}}\right) \times 100$$

The results are summarized in Tables 6A and 6B.

TABLE 6A

| IL-2 (50 U/ml) | Test substance | Dose (µg/ml) | optical density (OD$_{570}$) | Suppression (%) |
|---|---|---|---|---|
| — | — | — | 0.001 | — |
| + | — | — | 0.586 | — |
| + | compound of Example 1 | 0.001 | 0.508 | 13.3 |
| + | | 0.01 | 0.556 | 5.1 |
| + | | 0.1 | 0.009 | 98.6 |
| + | | 1 | 0.005 | 99.3 |
| + | compound of Example 2 | 0.001 | 0.555 | 5.3 |
| + | | 0.01 | 0.543 | 7.4 |
| + | | 0.1 | 0.558 | 4.8 |
| + | | 1 | 0.161 | 72.6 |
| + | compound of Example 3 | 0.001 | 0.551 | 6.0 |
| + | | 0.01 | 0.449 | 23.4 |
| + | | 0.1 | 0.471 | 19.7 |
| + | | 1 | 0.152 | 74.2 |

TABLE 6B

| IL-2 (50 U/ml) | Test substance | Dose (µg/ml) | optical density (OD$_{570}$) | Suppression (%) |
|---|---|---|---|---|
| — | — | — | 0.026 | — |
| + | — | — | 0.961 | — |
| + | compound of Example 2 | 0.001 | 0.898 | 6.7 |
| + | | 0.01 | 0.880 | 8.7 |
| + | | 0.1 | 0.774 | 20.0 |
| + | | 1 | 0.508 | 48.4 |
| + | compound of Example 5 | 0.01 | 0.915 | 4.9 |
| + | | 0.1 | 0.322 | 68.3 |
| + | | 1 | 0.239 | 77.2 |

As shown in Tables 6A and 6B, it was indicated that the compounds of the present invention strongly suppressed the proliferation of CTLL-2 cells induced by recombinant human IL-2.

EXPERIMENT EXAMPLE 7

Suppression of the IL-1, IL-2 and IL-4 Response of Mouse Thymocytes

The thymus was resected from 6-week-old male C3H/HeN mice, and a single cell suspension was prepared using the serum-free RPMI1640 culture medium. After washing three times, the cell suspension was adjusted to a concentration of $1.5 \times 10^7$ cells/ml in the RPMI1640 culture medium supplemented with $10^{-4}$M 2-mercaptoethanol and 20% FCS. One hundred µl of this cell suspension and 100 μl of the test substance were added to a 96-well flat-bottomed microtest plate, and cultured in the presence of 1 μg/ml of phytohemagglutinin (PHA) and human recombinant IL-1α, human recombinant IL-2 or mouse recombinant IL-4 at 37° C. in an atmosphere of 5% carbon dioxide and 95% air for 54 hours. After termination of culture, 18.5 KBq/well of $^3$H-thymidine was added thereto. After culturing the suspension for further 18 hours, the cells were harvested by a cell harvester, and the radioactivity incorporated into the cells was measured by a liquid scintillation counter, which was used as an index of IL-1, IL-2 or IL-4 response. The suppression of IL-1, IL-2 or IL-4 response was evaluated by calculating the percent suppression by the following formula.

$$\text{percent suppression (\%)} = \left(1 - \frac{\text{cpm, with interleukin and test substance} - \text{cpm, without interleukin}}{\text{cpm, with interleukin} - \text{cpm, without interleukin}}\right) \times 100$$

The results are summarized in Tables 7A, 7B and 7C.

TABLE 7A

| IL-1 (50 U/ml) | Test substance | Dose (μg/ml) | $^3$H-thymidine uptake (cpm) | Suppression (%) |
|---|---|---|---|---|
| — | — | — | 172 ± 18 | — |
| + | — | — | 11617 ± 720 | — |
| + | compound of Example 5 | 0.0001 | 10320 ± 1490 | 11.3 |
| + | | 0.001 | 7756 ± 686 | 33.7 |
| + | | 0.01 | 1239 ± 548 | 90.7 |
| + | | 0.1 | 595 ± 144 | 96.3 |
| + | | 1 | 419 ± 36 | 97.8 |

TABLE 7B

| IL-2 (U/ml) | Test substance | Dose (μg/ml) | $^3$H-thymidine uptake (cpm) | Suppression (%) |
|---|---|---|---|---|
| — | — | — | 360 | — |
| 10 | — | — | 2800 | — |
| 10 | compound of Example 5 | 0.0001 | 2810 | 0 |
| 10 | | 0.001 | 1660 | 46.7 |
| 10 | | 0.01 | 1285 | 62.1 |
| 10 | | 0.1 | 1125 | 68.6 |
| 10 | | 1 | 1300 | 61.5 |
| 50 | — | — | 60183 | — |
| 50 | compound of Example 5 | 0.0001 | 63715 | 0 |
| 50 | | 0.001 | 57600 | 4.5 |
| 50 | | 0.01 | 32955 | 45.5 |
| 50 | | 0.1 | 24600 | 59.4 |
| 50 | | 1 | 25525 | 58.0 |

TABLE 7C

| IL-4 (U/ml) | Test substance | Dose (μg/ml) | $^3$H-thymidine uptake (cpm) | Suppression (%) |
|---|---|---|---|---|
| — | — | — | 222 | — |
| 50 | — | — | 2182 | — |
| 50 | compound of Example 5 | 0.0001 | 3190 | 0 |
| 50 | | 0.001 | 2025 | 8.0 |
| 50 | | 0.01 | 1385 | 40.6 |
| 50 | | 0.1 | 815 | 69.7 |
| 50 | | 1 | 885 | 66.2 |
| 250 | — | — | 52761 | — |
| 250 | compound of Example 5 | 0.0001 | 45895 | 13.1 |
| 250 | | 0.001 | 39150 | 26.0 |
| 250 | | 0.01 | 33515 | 36.8 |
| 250 | | 0.1 | 24655 | 46.3 |
| 250 | | 1 | 21250 | 60.2 |

As shown in these Tables, it was indicated that the compounds of the present invention strongly suppressed proliferation of mouse thymocytes induced by IL-1, IL-2 or IL-4.

EXPERIMENT EXAMPLE 8

Suppression of Mouse Anti-Sheep Red Blood Cell Antibody Production

Male 5- to 7-week-old BALB/c mice were immunized with sheep red blood cells (5×10$^7$ cells/mouse, intravenous administration), and the test substance was administered intraperitoneally at the dose of 3 to 10 mg/kg/day for 4 consecutive days from the day of immunization. Four days after immunization, the spleen was resected, and suppression of anti-sheep red blood cell antibody production was examined by counting the number of plaque-forming cells (PFC) by direct plaque method using sheep red blood cells and guinea pig complement. At the same time, the body weight of the mouse, wet weight of the thymus and the spleen, and the number of spleen cells were also determined. The results are summarized in Table 8.

TABLE 8

| Test Substance | None added | Compound of Example 2 | Compound of Example 2 |
|---|---|---|---|
| Dose (mg/kg/day) | — | 3 | 10 |
| Number of animals | 7 | 5 | 5 |
| Body weight (g) on immunized day | 22 ± 1 | 22 ± 1 | 22 ± 1 |
| Body weight (g) at 4 days later | 24 ± 1 | 24 ± 1 | 23 ± 1 |
| Wet weight (mg) of thymus | 249 ± 39 | 318 ± 42 | 233 ± 25 |
| Wet weight (mg) of spleen | 68 ± 10 | 58 ± 11 | 58 ± 10 |
| Number of spleen cells (× 10$^8$ cell) | 2.7 ± 0.6 | 3.3 ± 0.5 | 2.5 ± 0.2 |
| Number of PFC | | | |
| × 10$^3$/1 × 10$^7$ cell | 8.7 ± 2.6 | 5.5 ± 0.8 | 4.0 ± 2.0 |
| Suppression (%) | — | 36.8 | 54.9 |
| × 10$^4$/spleen | 23.3 ± 6.6 | 17.9 ± 3.6 | 10.2 ± 5.5 |
| Suppression (%) | — | 23.2 | 56.2 |

As shown in Table 8, it is evident that the compound of Example 2 exhibits suppressive effect on anti-sheep red blood cell antibody production, that is, the effect of decreasing PFC number per unit spleen cells (1×10$^7$ cells) and PFC number per total spleen cells.

EXPERIMENT EXAMPLE 9

Suppression of Allo-Reactive Cytotoxic T Cells Induced by Immunization of Mouse Allogenic Cells Male 5- to 7-week-old BALB/c mice (H-2$^d$) were immunized with leukemia cell EL4 derived from C57BL/6 mice (H-2$^b$) (10$^7$ cells/mouse, intraperitoneal administration), and the test substance was administered intraperitoneally 5 times at the doses of 0.001 to 3 mg/kg/day or orally at the doses of 0.3 to 10 mg/kg/day from the day of immunization. Nine to ten days after immunization, the spleen was resected from the mice to prepare a single cell suspension and the suspension was used as effector cell suspension. The $^{51}$Cr-release assay was carried out in the same way as in Experiment Example 3, using EL4 cells as the target cells to measure the cytotoxic activity.

The activity of allo-reactive cytotoxic T cell is indicated by lytic unit (LU) per spleen. One lytic unit (LU) is defined as the number of effector cells required to cause 25% lysis of $5 \times 10^3$ target cells. At the same time, the body weight of mouse and number of spleen cells were also determined.

The results are shown in Tables 9A and 9B.

TABLE 9A

| Immunizing substance | Test substance | Dose (mg/kg/day) | Administration route | Number of animals | Body weight (g) 9 days after immunization | Number of spleen cells ($\times 10^8$ cell) | Cytotoxic T cell activity | |
|---|---|---|---|---|---|---|---|---|
| | | | | | | | LU/spleen | Suppression (%) |
| — | — | — | — | 2 | 28.5 | 1.0 | <50 | — |
| EL4 cell suspension | — | — | — | 6 | 27.5 ± 2.1 | 2.3 ± 0.7 | 1012 ± 328 | — |
| EL4 cell suspension | compound of Ex. 2 | 0.01 | ip × 5 | 6 | 29.0 ± 1.7 | 3.2 ± 0.5 | 724 ± 202* | 28.5 |
| EL4 cell suspension | compound of Ex. 2 | 0.03 | ip × 5 | 6 | 28.5 ± 1.0 | 2.6 ± 0.6 | 536 ± 272* | 47.0 |
| EL4 cell suspension | compound of Ex. 2 | 0.1 | ip × 5 | 6 | 28.3 ± 1.4 | 2.8 ± 0.5 | 527 ± 172* | 47.9 |
| EL4 cell suspension | compound of Ex. 2 | 0.3 | ip × 5 | 6 | 29.0 ± 1.8 | 3.1 ± 0.5 | 525 ± 58** | 48.1 |
| EL4 cell suspension | compound of Ex. 2 | 1 | iP × 5 | 6 | 27.3 ± 1.9 | 3.2 ± 0.6 | 318 ± 128* | 68.6 |
| EL4 cell suspension | compound of Ex. 2 | 3 | iP × 5 | 5 | 28.6 ± 1.7 | 2.7 ± 0.4 | <50** | 95.1 |

*$p < 0.05$
**$p$ 0.01
ip × 5 means 5 times' intraperitoneal administration

TABLE 9B

| Immunizing substance | Test substance | Dose (mg/kg/day) | Administration route | Number of animals | Body weight (g) 9 days after immunization | Number of spleen cells ($\times 10^8$ cell) | Cytotoxic T cell activity | |
|---|---|---|---|---|---|---|---|---|
| | | | | | | | LU/spleen | Suppression (%) |
| — | — | — | — | 2 | 28.5 | 1.4 | <50 | — |
| EL4 cell suspension | — | — | — | 6 | 28.2 ± 0.8 | 1.5 ± 0.4 | 922 ± 59.5 | — |
| EL4 cell suspension | compound of Ex. 2 | 0.3 | po × 5 | 5 | 28.0 ± 0.7 | 1.4 ± 0.2 | 323 ± 97 | 65.0 |
| EL4 cell suspension | compound of Ex. 2 | 1 | po × 5 | 5 | 29.0 ± 1.7 | 1.4 ± 0.3 | 473 ± 92 | 48.7 |
| EL4 cell suspension | compound of Ex. 2 | 3 | po × 5 | 5 | 29.4 ± 1.5 | 2.0 ± 0.3 | 427 ± 100 | 53.7 |
| EL4 cell suspension | compound of Ex. 2 | 10 | po × 5 | 5 | 27.4 ± 1.7 | 1.6 ± 0.3 | 274 ± 82 | 70.3 |

*$p < 0.05$
**$p < 0.01$
po × 5 means 5 times' oral administration

TABLE 9C

| Immunizing substance | Test substance | Dose (mg/kg/day) | Administration route | Number of animals | Body weight (g) 9 days after immunization | Number of spleen cells ($\times 10^8$ cell) | Cytotoxic T cell activity | |
|---|---|---|---|---|---|---|---|---|
| | | | | | | | LU/spleen | Suppression (%) |
| — | — | — | — | 2 | 27.0 | 0.6 | <50 | — |
| EL4 cell suspension | — | — | — | 5 | 24.4 ± 0.9 | 2.4 ± 0.2 | 1170 ± 471 | — |
| EL4 cell suspension | compound of Ex. 5 | 0.001 | ip × 5 | 5 | 23.6 ± 1.1 | 1.8 ± 0.2 | 589 ± 415 | 49.7 |
| EL4 cell suspension | compound of Ex. 5 | 0.003 | ip × 5 | 5 | 22.8 ± 1.6 | 1.8 ± 0.2 | 473 ± 265* | 59.6 |
| EL4 cell suspension | compound of Ex. 5 | 0.01 | ip × 5 | 5 | 24.4 ± 1.1 | 2.2 ± 0.3 | 443 ± 141* | 62.1 |
| EL4 cell suspension | compound of Ex. 5 | 0.03 | ip × 5 | 5 | 24.0 ± 2.2 | 2.1 ± 0.5 | 352 ± 148* | 69.9 |
| EL4 cell suspension | compound of Ex. 5 | 0.1 | ip × 5 | 5 | 25.4 ± 1.9 | 1.9 ± 0.3 | 158 ± 86** | 86.5 |
| EL4 cell suspension | compound of Ex. 5 | 0.3 | ip × 5 | 5 | 26.0 ± 1.6 | 1.9 ± 0.2 | <50** | >95 |

*$p < 0.05$
**$p < 0.01$
ip × 5 means 5 times' intraperitoneal administration

TABLE 9D

| Immunizing substance | Test substance | Dose (mg/kg/day) | Administration route | Number of animals | Body weight (g) 10 days after immunization | Number of spleen cells ($\times 10^8$ cell) | Cytotoxic T cell activity | |
|---|---|---|---|---|---|---|---|---|
| | | | | | | | LU/spleen | Suppression (%) |
| EL4 cell suspension | — | — | — | 4 | 25.3 ± 1.0 | 1.5 ± 0.2 | 1531 ± 525 | — |
| EL4 cell suspension | compound of Ex. 5 | 0.001 | po × 5 | 4 | 24.5 ± 1.7 | 1.5 ± 0.2 | 1929 ± 630 | 0 |
| EL4 cell suspension | compound of Ex. 5 | 0.003 | po × 5 | 5 | 24.6 ± 1.1 | 1.6 ± 0.3 | 1069 ± 400 | 30.2 |
| EL4 cell suspension | compound of Ex. 5 | 0.01 | po × 5 | 5 | 25.8 ± 1.3 | 1.6 ± 0.3 | 709 ± 189* | 53.7 |
| EL4 cell suspension | compound of Ex. 5 | 0.03 | po × 5 | 5 | 25.0 ± 1.2 | 1.6 ± 0.3 | 684 ± 181* | 55.3 |
| EL4 cell suspension | compound of Ex. 5 | 0.1 | po × 5 | 5 | 25.2 ± 0.4 | 1.7 ± 0.4 | 638 ± 155* | 58.3 |
| EL4 cell suspension | compound of Ex. 5 | 0.3 | po × 5 | 5 | 25.4 ± 0.5 | 1.6 ± 0.3 | 609 ± 197** | 60.2 |
| EL4 cell suspension | compound of Ex. 5 | 1 | po × 5 | 4 | 25.0 ± 1.4 | 1.7 ± 0.3 | 421 ± 12** | 72.5 |

*p < 0.05
**p < 0.01
po × 5 means 5 times' oral administration

TABLE 9E

| Immunizing substance | Test substance | Dose (mg/kg/day) | Administration route | Number of animals | Body weight (g) 10 days after immunization | Number of spleen cells ($\times 10^8$ cell) | Cytotoxic T cell activity | |
|---|---|---|---|---|---|---|---|---|
| | | | | | | | LU/spleen | Suppression (%) |
| EL4 cell suspension | — | — | — | 5 | 25.0 ± 0.7 | 1.1 ± 0.2 | 2785 ± 619 | — |
| EL4 cell suspension | compound of Ex. 5 | 0.003 | po × 10 | 5 | 25.0 ± 0.7 | 1.3 ± 0.3 | 1936 ± 840 | 30.5 |
| EL4 cell suspension | compound of Ex. 5 | 0.01 | po × 10 | 5 | 25.2 ± 1.3 | 1.4 ± 0.2 | 996 ± 279** | 64.2 |
| EL4 cell suspension | compound of Ex. 5 | 0.03 | po × 10 | 5 | 24.2 ± 1.3 | 1.5 ± 0.3 | 799 ± 304** | 71.3 |
| EL4 cell suspension | compound of Ex. 5 | 0.1 | po × 10 | 5 | 25.0 ± 0.7 | 1.4 ± 0.4 | 731 ± 318** | 73.8 |
| EL4 cell suspension | compound of Ex. 5 | 0.3 | po × 10 | 5 | 24.2 ± 1.3 | 1.6 ± 0.3 | 651 ± 257** | 76.6 |
| EL4 cell suspension | compound of Ex. 5 | 1 | po × 10 | 5 | 22.4 ± 0.5 | 1.5 ± 0.3 | 269 ± 179** | 90.3 |

*p < 0.05
**p < 0.01
po × 5 means 5 times' oral administration

TABLE 9F

| Immunizing substance | Test substance | Dose (mg/kg/day) | Administration route | Number of animals | Body weight (g) 10 days after immunization | Number of spleen cells ($\times 10^8$ cell) | Cytotoxic T cell activity | |
|---|---|---|---|---|---|---|---|---|
| | | | | | | | LU/spleen | Suppression (%) |
| EL4 cell suspension | — | — | — | 5 | 26.2 ± 1.1 | 1.8 ± 0.3 | 6784 ± 890 | — |
| EL4 cell suspension | sodium salt of compound of Ex. 2 | 0.03 | ip × 5 | 5 | 27.4 ± 2.1 | 1.8 ± 0.4 | 1133 ± 306** | 83.3 |
| EL4 cell suspension | sodium salt of compound of Ex. 2 | 0.1 | ip × 5 | 5 | 27.0 ± 2.0 | 1.8 ± 0.4 | 565 ± 93** | 91.7 |
| EL4 cell suspension | sodium salt of compound of Ex. 2 | 0.3 | ip × 5 | 5 | 22.0 ± 1.2 | 1.0 ± 0.5 | 131 ± 52** | 98.1 |

*p < 0.05
**p < 0.01
ip × 5 means 5 times' intraperitoneal administration

TABLE 9G

| Immunizing substance | Test substance | Dose (mg/kg/day) | Administration route | Number of animals | Body weight (g) 10 days after immunization | Number of spleen cells ($\times 10^8$ cell) | Cytotoxic LU/spleen | T cell activity Suppression (%) |
|---|---|---|---|---|---|---|---|---|
| EL4 cell suspension | — | — | — | 7 | 26.2 ± 1.1 | 1.6 ± 0.4 | 2222 ± 647 | — |
| EL4 cell suspension | sodium salt of compound | 0.003 | iv × 9 | 7 | 27.4 ± 2.1 | 1.5 ± 0.2 | 1083 ± 465** | 51.3 |

TABLE 9G-continued

| Immunizing substance | Test substance | Dose (mg/kg/day) | Administration route | Number of animals | Body weight (g) 10 days after immunization | Number of spleen cells ($\times 10^8$ cell) | Cytotoxic LU/spleen | T cell activity Suppression (%) |
| --- | --- | --- | --- | --- | --- | --- | --- | --- |
| EL4 cell suspension | sodium salt of compound of Ex. 2 | 0.01 | iv × 9 | 7 | 27.0 ± 2.0 | 1.5 ± 0.3 | 489 ± 217** | 78.0 |
| EL4 cell suspension | sodium salt of compound of Ex. 2 | 0.03 | iv × 9 | 7 | 22.0 ± 1.2 | 1.7 ± 0.3 | 298 ± 209** | 86.6 |
| EL4 cell suspension | sodium salt of compound of Ex. 2 | 0.1 | iv × 9 | 7 | 23.8 ± 1.3 | 1.1 ± 0.1 | 282 ± 79** | 87.3 |
| EL4 cell suspension | sodium salt of compound of Ex. 2 | 0.3 | iv × 9 | 7 | 23.6 ± 3.4 | 1.3 ± 0.1 | 65 ± 39** | 97.1 |

**p <0.01
iv × 9 means 9 times' intravenous administration

As shown in Tables 9A and 9B, it is evident that 5 times of intraperitoneal or oral administration of the compound of Example 2 strongly suppresses the induction of allo-reactive cytotoxic T cells in spleen cells of a mouse immunized with allogenic cells. In the meantime, the suppression of increase of weight or significant decrease of the number of spleen cells was not observed.

As shown in Tables 9C and 9E, it is evident that the intraperitoneal or oral administration of the compound of Example 5 for five times strongly suppresses the induction of allo-reactive cytotoxic T cells in spleen cells of a mouse immunized with allogenic cells and that 10 times of oral administration of said compound exhibits significant suppressive activity up to the dose of 0.03 mg/kg.

As is evident from the results shown in Table 9F, the sodium salt of the compound of Example 5 showed the suppressive activity almost equivalent to that of the compound of Example 5 other than sodium salt in the induction of allo-reactive cytotoxic T cells in spleen cells of a mouse immunized with allogenic cells.

EXPERIMENT EXAMPLE 10

Suppression of allo-reactive cytotoxicity-specific antibody production induced by allogenic cell immunization of mouse Male 5- to 7-week-old BALB/c mice were immunized with leukemia cell EL4 derived from C57BL/6 mice ($10^7$ cells/mouse, intraperitoneal administration) in the same way as in Experiment Example 9, and the test substance was administered intraperitoneally or orally at the doses of 0.001 to 3 mg/kg/day from the day of immunization. Nine to ten days after immunization, a serum was collected from the mice. Fifty μl of the two-fold serial dilution of the serum, 50 μl of a guinea pig complement and EL4 cell suspension labelled with $^{51}$Cr as the target cell ($5 \times 10^4$ cells/ml, 100 μl) were together added to a 96-well microtest plate. After incubation at 37° C. for 1 hour, the amount of $^{51}$Cr released in the supernatant was measured, and the complement-dependent cytotoxicity was calculated by the following formula.

$$\text{cytotoxicity} (\%) = \left(1 - \frac{cpm, \text{serum} + \text{target cells} + \text{complement} - cpm, \text{complement} + \text{target cells}}{cpm, \text{total radioactivity of target cells} - cpm, \text{complement} + \text{target cells}}\right) \times 100$$

The value of allo-specific cytotoxic antibody determined as above was expressed by the titer calculated on the basis of the concentration at which the releasing amount of $^{51}$Cr was 50% of that of $^{51}$Cr-labelled target cells treated with 0.1 N HCl.

TABLE 10A

| Immunizing substance | Test substance | Dose (mg/kg/day) | Administration route | Number of animals | Allogenic cell-specific antibody in serum | |
| --- | --- | --- | --- | --- | --- | --- |
| | | | | | Titer | Suppression (%) |
| — | — | — | — | 2 | <16 | — |
| EL4 cell suspension | — | — | — | 6 | 82 ± 19 | — |
| EL4 cell suspension | compound of Ex. 2 | 0.01 | ip × 5 | 6 | 119 ± 47 | 0 |
| EL4 cell suspension | compound of Ex. 2 | 0.03 | ip × 5 | 6 | 87 ± 55 | 0 |
| EL4 cell suspension | compound of Ex. 2 | 0.1 | ip × 5 | 6 | 89 ± 32 | 0 |
| EL4 cell suspension | compound of Ex. 2 | 0.3 | ip × 5 | 6 | 50 ± 48 | 39.9 |
| EL4 cell suspension | compound of Ex. 2 | 1 | ip × 5 | 6 | <16** | >80 |
| EL4 cell suspension | compound of Ex. 2 | 3 | ip × 5 | 5 | <16** | >80 |

*p <0.05
**p <0.01
ip × 5 means 5 times' intraperitoneal administration

TABLE 10B

| Immunizing substance | Test substance | Dose (mg/kg/day) | Administration route | Number of animals | Allogenic cell-specific antibody in serum | |
|---|---|---|---|---|---|---|
| | | | | | Titer | Suppression (%) |
| EL4 cell suspension | — | — | — | 2 | 214 ± 75 | — |
| EL4 cell suspension | compound of Ex. 2 | 0.3 | po × 5 | 6 | 130 ± 45 | 39.3 |
| EL4 cell suspension | compound of Ex. 2 | 1 | po × 5 | 5 | 133 ± 50 | 37.9 |
| EL4 cell suspension | compound of Ex. 2 | 3 | po × 5 | 5 | 88 ± 47* | 58.9 |
| EL4 cell suspension | compound of Ex. 2 | 10 | po × 5 | 5 | 67 ± 16** | 68.7 |

*$p < 0.05$
**$p < 0.01$
po × 5 means 5 times' oral administration

TABLE 10C

| Immunizing substance | Test substance | Dose (mg/kg/day) | Administration route | Number of animals | Allogenic cell-specific antibody in serum | |
|---|---|---|---|---|---|---|
| | | | | | Titer | Suppression (%) |
| EL4 cell suspension | — | — | — | 4 | 299 ± 129 | — |
| EL4 cell suspension | compound of Ex. 5 | 0.01 | po × 5 | 5 | 318 ± 75 | 0 |
| EL4 cell suspension | compound of Ex. 5 | 0.03 | po × 5 | 5 | 186 ± 100 | 37.8 |
| EL4 cell suspension | compound of Ex. 5 | 0.1 | po × 5 | 5 | 115 ± 19* | 61.5 |
| EL4 cell suspension | compound of Ex. 5 | 0.3 | po × 5 | 5 | 91 ± 67* | 69.6 |
| EL4 cell suspension | compound of Ex. 5 | 1 | po × 5 | 4 | 52 ± 27* | 82.5 |

*$p < 0.05$
**$p < 0.01$
po × 5 means 5 times' oral administration

TABLE 10D

| Immunizing substance | Test substance | Dose (mg/kg/day) | Administration route | Number of animals | Allogenic cell-specific antibody in serum | |
|---|---|---|---|---|---|---|
| | | | | | Titer | Suppression (%) |
| EL4 cell suspension | — | — | — | 5 | 205 ± 56 | — |
| EL4 cell suspension | compound of Ex. 5 | 0.003 | po × 10 | 5 | 147 ± 43 | 28.3 |
| EL4 cell suspension | compound of Ex. 5 | 0.01 | po × 10 | 5 | 112 ± 66* | 45.4 |
| EL4 cell suspension | compound of Ex. 5 | 0.03 | po × 10 | 5 | 123 ± 43* | 40.0 |
| EL4 cell suspension | compound of Ex. 5 | 0.1 | po × 10 | 5 | 59 ± 38** | 71.2 |
| EL4 cell suspension | compound of Ex. 5 | 0.3 | po × 10 | 5 | 49 ± 26** | 76.1 |
| EL4 cell suspension | compound of Ex. 5 | 1 | po × 10 | 5 | 48 ± 37** | 76.6 |

*$p < 0.05$
**$p < 0.01$
po × 10 means 10 times' oral administration

TABLE 10E

| Immunizing substance | Test substance | Dose (mg/kg/day) | Administration route | Number of animals | Allogenic cell-specific antibody in serum | |
|---|---|---|---|---|---|---|
| | | | | | Titer | Suppression (%) |
| EL4 cell suspension | — | — | — | 5 | 189 ± 25 | — |
| EL4 cell suspension | sodium salt of compound of Ex. 5 | 0.03 | ip × 5 | 5 | 94 ± 14* | 50.3 |
| EL4 cell suspension | sodium salt of compound of Ex. 5 | 0.1 | ip × 5 | 5 | 50 ± 4** | 73.5 |
| EL4 cell | sodium | 0.3 | ip × 5 | 5 | 21 ± 8** | 88.9 |

TABLE 10E-continued

| Immunizing substance | Test substance | Dose (mg/kg/day) | Administration route | Number of animals | Allogenic cell-specific antibody in serum | |
|---|---|---|---|---|---|---|
| | | | | | Titer | Suppression (%) |
| suspension | salt of compound of Ex. 5 | | | | | |

*p <0.05
**p <0.01
ip × 5 means 5 times' intraperitoneal administration

TABLE 10F

| Immunizing substance | Test substance | Dose (mg/kg/day) | Administration route | Number of animals | Allogenic cell-specific antibody in serum | |
|---|---|---|---|---|---|---|
| | | | | | Titer | Suppression (%) |
| EL4 cell suspension | — | — | — | 7 | 251 ± 61 | — |
| EL4 cell suspension | sodium salt of Ex. 5 | 0.003 | iv × 9 | 7 | 236 ± 76 | 6.0 |
| EL4 cell suspension | sodium salt of Ex. 5 | 0.01 | iv × 9 | 7 | 152 ± 27** | 39.4 |
| EL4 cell suspension | sodium salt of Ex. 5 | 0.03 | iv × 9 | 7 | 79 ± 50** | 68.5 |
| EL4 cell suspension | sodium salt of Ex. 5 | 0.1 | iv × 9 | 7 | 40 ± 23** | 84.1 |
| EL4 cell suspension | sodium salt of Ex. 5 | 0.3 | iv × 9 | 7 | 46 ± 11** | 81.7 |

**p <0.01
iv × 9 means 9 times' intravenous administration

As shown in Tables 10A to 10D, it is evident that the intraperitoneal or oral administration of the compounds of Example 2 and Example 5 strongly suppresses allospecific cytotoxic antibody production in serum of a mouse immunized with allogenic cells.

As is evident from the results shown in Table 10E, the sodium salt of the compound of Example 5 showed the suppressive activity almost equivalent to that of the compound of Example 5 other than sodium salt in the production of allo-specific cytotoxic antibody in serum of a mouse immunized with allogenic cells.

EXPERIMENT EXAMPLE 11

Suppression of mouse acute graft versus host reaction (GVHR)

C57BL/6 mouse spleen cell suspension ($2 \times 10^7$ cells/mouse) was injected into the right hind footpad of 5- to 7-week-old $BDF_1$ female mice. Seven days after injection, right popliteal lymph node was resected to measure the weight thereof and compare the weight with that of the left popliteal lymph node of the control mice injected with physiological saline, which was used as an index of acute graft versus host reaction (GVHR). The compound of Example 5 was administered intraperitoneally at the dose of 0.3 mg/kg, orally at the dose of 1 mg/kg and intramuscularly at the doses of 0.3 and 1 mg/kg for 6 days from the day of injection, and at the seventh day, the weight of the right poples lymphonodus was measured.

As the results show in Table 11, it is evident that intraperitoneal, oral or intramuscular administration of the compound of Example 5 strongly suppresses the mouse acute graft versus host reaction (GVHR).

TABLE 11

| Sole injection | Test substance | Dose (mg/kg/day) | Administration route | Number of animals | Body weight (g) 7 days after injection | Popliteal lymph node weight (mg) | Suppression (%) |
|---|---|---|---|---|---|---|---|
| — | — | — | — | 5 | 19.8 ± 0.8 | 0.80 ± 0.12 | — |
| C57BL/6 mouse spleen cell | — | — | — | 5 | 19.8 ± 0.8 | 7.20 ± 1.96 | — |
| C57BL/6 mouse spleen cell | compound of Example 5 | 0.3 | ip × 6 | 5 | 19.0 ± 2.2 | 4.46 ± 1.72* | 38.1 |
| C57BL/6 mouse spleen cell | compound of Example 5 | 1 | po × 6 | 5 | 20.4 ± 0.6 | 3.30 ± 0.64** | 54.2 |
| C57BL/6 mouse spleen cell | compound of Example 5 | 0.3 | im × 6 | 5 | 20.0 ± 0.7 | 2.88 ± 0.58** | 60.0 |
| C57BL/6 mouse spleen cell | compound of Example 5 | 1 | im × 6 | 5 | 18.8 ± 1.3 | 2.28 ± 0.48** | 68.3 |

*p <0.05
**p <0.01
ip × 6 means 6 times' intraperitoneal administrations, po × 6 means 6 times' oral administrations and im × 6 means 6 times' intramuscular administration

EXPERIMENT EXAMPLE 12

Cytotoxicity to various cultured tumor cell lines

Cytotoxicity to various human tumor cell lines was examined as follows:

Cells of human cell lines, K562, MOLT4, U937 and HL60 were respectively suspended to the concentration of $4 \times 10^5$ cells/ml in the RPMI1640 culture medium supplemented with 20% FCS. Fifty μl of each suspension was added to each well of a 96-well microtest plate to which 50 μl of the test solution had been added. After culturing the suspension at 37° C. in an atmosphere of 5% carbon dioxide for 72 hours, the absorbancy at 570 nm was measured in the same way as with the colorimetry using MTT in Experiment Example 1, and the percent suppression was calculated by the following formula, which was used as an index of cytotoxicity.

$$\text{percent suppression (\%)} = \left(1 - \frac{\text{absorbancy with test substance}}{\text{absorbancy without test substance}}\right) \times 100$$

TABLE 12A

| Cell lines | Compound of Example 2 | | |
|---|---|---|---|
| | Dose (μg/ml) | Absorbancy | Suppression (%) |
| K562 | 0 | 1.136 ± 0.020 | — |
| | 0.1 | 1.128 ± 0.025 | 0.7 |
| | 1 | 1.103 ± 0.045 | 2.9 |
| | 10 | 1.086 ± 0.045 | 4.4 |
| MOLT4 | 0 | 1.154 ± 0.016 | — |
| | 0.1 | 1.144 ± 0.040 | 0.9 |
| | 1 | 1.027 ± 0.009 | 11.0 |
| | 10 | 1.045 ± 0.041 | 9.4 |
| U937 | 0 | 0.682 ± 0.034 | — |
| | 0.1 | 0.669 ± 0.030 | 1.9 |
| | 1 | 0.681 ± 0.009 | 0.1 |
| | 10 | 0.673 ± 0.111 | 1.3 |
| HL60 | 0 | 1.490 ± 0.057 | — |
| | 0.1 | 1.385 ± 0.066 | 7.0 |
| | 1 | 1.466 ± 0.126 | 1.6 |
| | 10 | 1.441 ± 0.018 | 3.3 |

TABLE 12B

| Cell lines | Compound of Example 4 | | |
|---|---|---|---|
| | Dose (μg/ml) | Absorbancy | Suppression (%) |
| K562 | 0 | 1.136 ± 0.020 | — |
| | 0.1 | 1.145 ± 0.038 | 0 |
| | 1 | 1.129 ± 0.021 | 0.6 |
| | 10 | 1.148 ± 0.032 | 0 |
| MOLT4 | 0 | 1.154 ± 0.016 | — |
| | 0.1 | 1.026 ± 0.026 | 11.0 |
| | 1 | 1.037 ± 0.027 | 10.1 |
| | 10 | 1.014 ± 0.055 | 12.1 |
| U937 | 0 | 0.682 ± 0.034 | — |
| | 0.1 | 0.765 ± 0.033 | 0 |
| | 1 | 0.744 ± 0.017 | 0 |
| | 10 | 0.750 ± 0.048 | 0 |
| HL60 | 0 | 1.490 ± 0.057 | — |
| | 0.1 | 1.401 ± 0.028 | 6.0 |
| | 1 | 1.493 ± 0.031 | 0 |
| | 10 | 1.368 ± 0.087 | 8.2 |

TABLE 12C

| Cell lines | Compound of Example 5 | | |
|---|---|---|---|
| | Dose (μg/ml) | Absorbancy | Suppression (%) |
| K562 | 0 | 1.136 ± 0.020 | — |
| | 0.1 | 1.111 ± 0.037 | 2.2 |
| | 1 | 1.090 ± 0.044 | 4.0 |
| | 10 | 1.083 ± 0.033 | 4.7 |
| MOLT4 | 0 | 1.154 ± 0.016 | — |
| | 0.1 | 1.031 ± 0.035 | 10.7 |
| | 1 | 1.013 ± 0.013 | 12.2 |
| | 10 | 0.967 ± 0.006 | 16.2 |
| U937 | 0 | 0.682 ± 0.034 | — |
| | 0.1 | 0.695 ± 0.032 | 0 |
| | 1 | 0.699 ± 0.044 | 0 |
| | 10 | 0.684 ± 0.038 | 0 |
| HL60 | 0 | 1.490 ± 0.057 | — |
| | 0.1 | 1.505 ± 0.035 | 0 |
| | 1 | 1.415 ± 0.010 | 5.0 |
| | 10 | 1.201 ± 0.061 | 19.4 |

As is evident from the results shown in Tables 12A to 12C, the cytotoxicity of the compounds of the present invention to the various cultured human tumor cell lines is weak, with the concentration of 50% inhibition (IC$_{50}$) being 10 μg/ml or more.

EXAMPLE 1

(i) Jar cultivation of *Myriococcum albomyces*

One hundred ml of the GCY medium (20 g of glucose, 5 g of corn steep liquor, 3 g of yeast extract and 0.5 g of MgSO$_4$.7H$_2$O in one liter, pH 6) was placed into each of two 500 ml long-neck shaking flasks, and autoclaved for sterilization at 121° C. for 20 minutes, followed by inoculation of about 1 cm$^2$ of mycelia of *Myriococcum albomyces* ATCC No. 16425 grown on the potato dextrose agar medium, which was then incubated at 40° C. for 3 days in a reciprocal shaker (135 rpm, amplitude: 8 cm). The resultant culture was inoculated as the seed into the 10 l-fermentation jar in which the GCY medium described above and 1 g of an antifoaming agent (F-18 manufactured by Dow Coning Co.) had been placed, which was then subjected to aerobic spinner culture (0.5 VVM, 300 rpm) at 40° C. for 7 days.

(ii) Collection of Compound (a) from the culture of *Myriococcum albomyces*

From 4.5 l of the culture obtained in (i), cells were removed and the culture filtrate was obtained. The culture filtrate (4 l) was allowed to pass through a column of Amberlite XAD-2 ($\phi$40 mm × h750 mm) so that Compound (a) could be adsorbed. The column was washed with 1 l of water. Then, 1 l of 30% methanol, 1 l of 50% methanol and 3 l of 80% methanol were allowed to pass in this order, and the eluate with 80% methanol containing Compound (a) was collected.

Separately, the cells were extracted 3 times with methanol of an amount about 5 times that of the wet weight of the cells, and water was added to the extract to give a 30% methanol solution, which was then allowed to flow through a column of Amberlite XAD-2 ($\phi$40 mm × h750 mm) so that Compound (a) could be adsorbed. One liter of 30% methanol, 1 l of 50% methanol and 3 l of 80% methanol were allowed to flow in this order, and the eluate with 80% methanol containing Compound (a) was collected.

The fractions eluted with 80% methanol from the culture filtrate and from the cells obtained as described above were combined, concentrated under reduced pressure, and freeze-dried to give 0.5 g of powders containing Compound (a).

(iii) Purification of Compound (a)

The powders (0.5 g) obtained in (ii) was dissolved in methanol and the same amount of water was added thereto to give 50% methanol solution. The solution was allowed to flow through a column of Amberlite XAD-2 (φ25 mm×h300 mm) and then each 500 ml of 30%, 50%, 60%, 70% and 75% methanol solution were allowed to flow through the column in this order. The eluate with 70 to 75% methanol containing Compound (a) was collected. Water was added to this solution to give 50% methanol solution, and purification by column chromatography on Amberlite XAD-2 was carried out again to give 28 mg of Compound (a), m.p. 145°–147° C.

$^1$H-NMR δ (ppm CD$_3$OD): 5.55 (m), 5.40 (m), 3.87 (m), 2.30 (t) IRν (KBr): 3300, 1625, 970 cm$^{-1}$

EXAMPLE 2

(1)

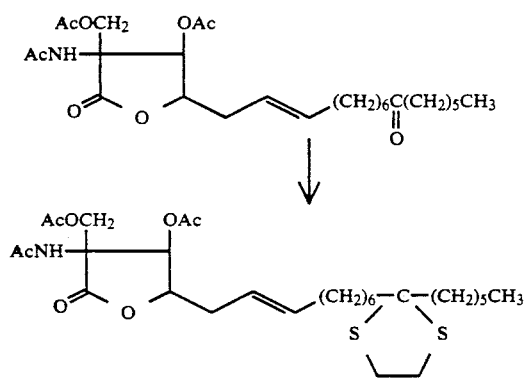

The Compound (2-i) (1509.5 mg) was dissolved in 12.5 ml of dry dichloromethane, to which 367 μl of 1,2-ethylenedithiol and 12.5 μl of trifluoroborane etherate were added, and stirred at room temperature for 47 hours. The reaction mixture was washed with 5% sodium bicarbonate and saturated sodium chloride, dried over magnesium sulfate, and concentrated under reduced pressure to give oily residue. The residue was purified by chromatography on silica gel (50 g) column (eluent: ethyl acetate:n-hexane=6:4), further purified by thin-layer chromatography (eluent: ethyl acetate:n-hexane=7:3), and the fractions of Rf 0.4 were concentrated under reduced pressure to give 1538.9 mg of Compound (2-ii) as colorless, transparent oil.

IRν$_{max}$$^{CHCl_3}$ (cm$^{-1}$): 3400, 2950, 2850, 2700, 1780, 1750, 1680, 1500, 1370, 1230, 1050.

$^1$HNMR (200 MHz, in CDCl$_3$, Ref. TMS) δ: 1H, 6.1 (br.s., -NHAc), 1H, 5.8 (d., J=4.64, 3-H), 1H, 5.6 (dt-t. like, J=15.38, 6.47, 7-H), 1H, 5.4 (dt-t. like, J=15.38, 6.60, 6-H), 1H, 4.7 (ddd., J=8.18, 5.37, 4.64, 4-H), 2H, 4.5 (s., 21-H$_2$), 4H, 3.3 (s., 1', 2'-H$_2$), 1H, 2.4 (ddd., J=14.89, 8.18, 6.60, 5-H), 1H, 2.3 (ddd., J=14.89, 6.60, 5.37, 5-H), 3H, 2.1 (s., Ac), 3H, 2.05 (s, Ac), 3H (s., 2.03), 2H, 2.0 (m., 8-H$_2$), 4H, 1.9 (m., 13,15-H$_2$), 16H, 1.55 (m), 1.30 (br., s.), 1.29 (br., s.) (9-12, 16-19-H$_2$), 3H, 0.9 (t., J=6.47, 20-H$_3$).

EI-MS m/z: 585, 500, 440, 398, 189, 160, 43.

(2)

Compound (2-ii)

-continued (2-iii)

AcOCH$_2$  OAc
AcNH—
O   O   (CH$_2$)$_{15}$CH$_3$

The Compound (2-ii) (1422.0 mg) was dissolved in 40 ml of dry ethanol, to which 22 g of Raney nickel was added, and refluxed under heating for 90 minutes. After cooling the reaction mixture to room temperature, Raney nickel was filtered off. This Raney nickel was washed with 200 ml of ethanol, and the washing and filtrate were combined and concentrated under reduced pressure to give 1062.7 mg of solid residue. Anhydrous acetic acid (5.0 ml) and 5.0 ml of pyridine were added thereto, and stirred overnight at room temperature. The reaction mixture was diluted with water and extracted with ethyl acetate. The ethyl acetate layer was washed with 1N hydrochloric acid, 5% sodium bicarbonate and saturated sodium chloride in order, and dried over magnesium sulfate. White foamy residue obtained by concentration under reduced pressure was purified by chromatography on silica gel (33 g) column (eluent: ethyl acetate:n-hexane=7:3). Further purification by thin-layer chromatography (eluent: ethyl acetate:n-hexane=7:3) was carried out, and the fractions of Rf 0.4 were collected and concentrated under reduced pressure to give 862.2 mg of the desired Compound (2-iii) as white foamy substance.

IRν$_{max}$$^{CHCl_3}$ (cm$^{-1}$): 3400, 2910, 2850, 1775, 1750, 1680, 1500, 1460, 1370, 1270, 1250, 1190, 1030.

$^1$HNMR (200 MHz, in CDCl$_3$, Ref. TMS) δ: 1H, 6.0 (br.s., -NHAc), 1H, 5.8 (d., J=4.39, 3-H), 1H, 4.7 (dt., J=9.03, 4.40, 4-H), 2H, 4.53 (s., 21-H$_2$), 3H, 2.10 (s., Ac), 3H, 2.05 (s, Ac), 3H, 2.03 (s., Ac), 4H, 1.65 (m., 5,6-H$_2$), 26H, 1.26 (br., s., 7-19-H), 3H, 0.88 (t., J=6.47, 20-H).

MS(EI-MS), m/z: 497, 454, 365, 322, 129, 43.

(3) The step from Compound (2-iii) to Compound (b)

The Compound (2-iii) (81.9 mg) was dissolved in 4.0 ml of methanol, to which 0.99 ml of 1N aqueous solution of sodium hydroxide was added, and refluxed under a nitrogen atmosphere overnight. The reaction mixture was neutralized with 1N hydrochloric acid, and the precipitated white insoluble substance was filtered with suction, followed by washing with methanol and water. The substance was dried and recrystallized from methanol to give 16.1 mg of Compound (b) as white crystals, m.p. 159.0°–161.0° C.

IRν$_{max}$$^{KBr}$ (cm$^{-1}$): 3380, 3200, 2910, 1620, 1460, 1100, 1060, 960.

$^1$HNMR (200 MHz, in CD$_3$OD) δ: 1H, 4.0 (d., J=11.12, 21-H), 1H, 3.9 (d., J=11.12, 21-H), 1H, 3.8 (br., t., J=7.08, 4-H), 1H, 3.7 (d., J=1.22, 3-H), 4H, 1.6 (m), 26H, 1.3 (br., s., 5-19-H), 3H, 0.9 (t., J=6.47, 20-H).

MS(FAB), m/z: 390, 372, 291, 277, 165, 104.

Compound (2-i) was synthesized as follows:

To 8.10 g of ISP-I, 65 ml of pyridine was added at room temperature, and 70 ml of anhydrous acetic acid was added thereto with vigorous stirring. Stirring was continued for about 1 hour. With complete dissolution of ISP-I, stirring was terminated and the mixture was kept standing overnight. To the reaction mixture was added ice water, and the mixture was extracted with ethyl acetate, followed by washing with 1N hydrochloric acid, 5% sodium bicarbonate and saturated sodium chloride in order. The organic layer was dried and the solvent was distilled off to give 10.08 g of oily residue. The residue was purified by chromatography on silica gel (300 g) column using a mixture of ethyl acetate:n-hexane=7:3 as an eluent. The eluate of 900 to 1700 ml was collected and concentrated under reduced pressure to give 9.29 g of Compound (2-i) as colorless, transparent oil (yield 91.4%).

IR$\nu_{max}$(CHCl$_3$) (cm$^{-1}$): 2930, 1760, 1690, 1380, 1220

$^1$HNMR (200 MHz, in CDCl$_3$, Ref:TMS), δ: 6.05 (1H, br., s., -NHAc), 5.79 (1H, d, J=4.4 Hz, 3-H), 5.57 (1H, dt.t-like, J=15.4, 6.3 Hz, 7-H), 5.38 (1H, dt.t-like, J=15.4, 6.4 Hz, 6-H), 4.72 (1H, ddd, J=7.6, 5.1, 4.6 Hz, 4-H), 4.51 (2H, s, 21-H$_2$), 2.5-2.2 (2H, m, 5-H$_2$), 2.38 (4H, t, J=7.5 Hz, 13-, 15-H$_2$), 2.10 (3H, s, -Ac), 2.05 (3H, s, -Ac), 2.03 (3H, s, -Ac), 2.1-1.9 (2H, m, 8-Hz), 1.55 (4H, qui., J=6.8 Hz, 12, 16-H$_2$), 1.27 (12H, br.s, 9-11, 17-19-H$_2$), 0.88 (3H, t., J=6.5 Hz, 20-H$_3$).

$^{13}$C-NMR (100 MHz, in CDCl$_3$, Ref:TMS), δ: 211.37 (s, 14-C), 172.32 (s, >C=O), 170.08 (s, >C=O), 169.27 (s, >C=O), 168.75 (s, >C=O), 135.04 (d, 6-C), 123.16 (d, 7-C), 81.62 (d, 4-C), 72.01 (d, 3-C), 62.75 (t, 21-C), 62.73 (s, 2-C), 42.85, 42.77 (each t, 13, 15-C), 32.46, 32.20, 31.63 (each t, 5-, 8-, 18-C), 29.11, 29.00, 28.97, 28.91, 23.91, 23.85 (each t, 9-12, 16, 17-C), 22.76 (q, -COMe), 22.50 (t, 19-C), 20.55 (q, -COMe), 20.31 (q, -COMe), 14.00 (q, 20-C).

EI-MS m/z: 509, 491, 382, 348, 279, 129, 43.

HREI-MS: C$_{27}$H$_{43}$NO$_8$ Calculated: 509.2990 Measured: 509.2998.

EXAMPLE 3

Synthesis of Compound (c)

The Compound (2-ii) (72.6 mg) was dissolved in 2.8 ml of methanol, to which 0.75 ml of 1N sodium hydroxide was added, and refluxed under a nitrogen atmosphere overnight. The reaction mixture was neutralized with 1N hydrochloric acid, and the solvent was distilled off under reduced pressure. Water was added thereto, and the insoluble substance was filtered with suction, washed with water, air-dried and dried under reduced pressure in a desiccator. The resultant white substance (23.3 mg) was dissolved in methanol with heating, and the insoluble substance was filtrated off. The filtrate was concentrated under reduced pressure to give white residue. The resultant residue was washed with ethyl acetate and dried to give 12.8 mg of Compound (c) as white substance, m.p. 167.0°-170.0° C.

$^1$HNMR (200 MHz, in CD$_3$OD) δ: 1H, 5.5 (dt-t. like, J$_d$=15.14, J$_t$=6.27, 7-H), 1H, 5.4 (dt-t. like, J$_d$=14.89, J$_t$=6.60, 6-H), 1H, 4.0 (d., J=10.99, 21-H), 1H, 3.9 (d., J=10.99, 21-H), 1H, 3.84 (br.t., J=7.00, 4-H), 1H, 3.79 (d., J=0.97, 3-H), 4H, 3.3 (s., -H), 2H, 2.3 (br.t., J=6.47, 5-H), 2H, 2.0 (dt., J$_d$=6.35, J$_t$=6.35, 8-H), 4H, 1.9 (m., 13, 15-H), 4H, 1.5 (m., 12, 16-H), 12H, 1.3 (m., 9-11, 17-19-H), 3H, 0.9 (t., J=6.60, 20-H).

EXAMPLE 4

Synthesis of Compound (d)

Sodium carbonate (26.9 mg) was dissolved in 1.5 ml of water, to which 35.0 mg of hydroxylamine hydrochloride and 3.5 ml of ethanol were added in order. The mixture was heated in a water bath at 70° C., to which 200.9 mg of ISP-I was added, and shaken to dissolve ISP-I. With complete dissolution of ISO-I, the mixture was heated for further 6 hours at the same temperature. After the pH was confirmed to be 7, the reaction mixture was concentrated under reduced pressure to dryness as it was. To the residue was added water and the insoluble substance was filtered with suction. The resultant white substance (183.6 mg) was dissolved in 9 ml of methanol with heating, cooled to room temperature and kept standing overnight. The precipitated white insoluble substance (unreacted ISP-I) was filtered off, and the residue obtained from the filtrate was recrystallized to give 87.8 mg of Compound (d) as white substance, m.p. 179.5°-180.5° C.

$[\alpha]_D^{28}$ = -5.78° (c=0.509, methanol).

IR$\nu_{max}^{KBr}$ (cm$^{-1}$): 3200, 2910, 1620, 1460, 1320, 1100, 1050, 965.

MS(EI-MS) m/z: 398, 328, 256, 128, 104, 18.

EXAMPLE 5

(1)

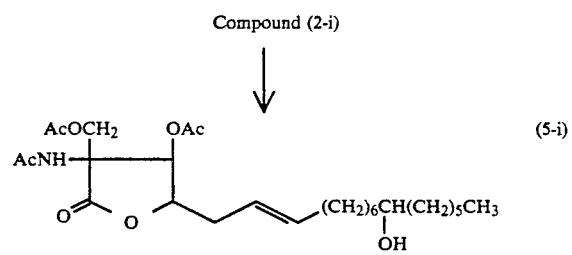

The Compound (2-i) (589.4 mg) was dissolved in 26 ml of dioxane, to which 10 ml of water was added. With stirring at room temperature, several small pieces of dry ice was added thereto, and with disappearance of solid, 116 mg of sodium borohydride was added to the mixture. The same procedure was repeated, and 20 minutes later, the solution was acidified with 1N hydrochloric acid (not more than pH 2). After 10 minutes' stirring, the solution was adjusted to weak-acidic or neutral with 1N sodium hydroxide and dioxane was distilled off by concentration under reduced pressure. To the residue was added water, and the mixture was extracted with ethyl acetate. The ethyl acetate layer was washed with 5% sodium bicarbonate and saturated sodium chloride in order and dried over magnesium sulfate. The residue (589.6 mg) obtained by concentration under reduced pressure was purified by chromatography on silica gel (30 g) column, eluted with a solution of chloroform:methanol=98:2, and further purified by thin-layer chromatography (eluent: chloroform:methanol=9:1). The fractions of Rf 0.4 were collected and concentrated under reduced pressure to give 386.3 mg of the desired Compound (5-i) as colorless, transparent oil. The fractions before and after those containing the desired compound were purified by preparative thin-layer chromatography respectively using the mixtures of chloroform:methanol=95:5 and ethyl acetate:n-hexane=8:2 as the eluents, and 30.2 mg of the desired compound was obtained from the band of Rf 0.4 as colorless, transparent oil.

IR$\nu_{max}^{CHCl_3}$ (cm$^{-1}$): 2910, 2850, 1775, 1750, 1685, 1500, 1370, 1220, 1030, 745.

$^1$HNMR (200 MHz, in CDCl$_3$, Ref. TMS) δ: 1H, 6.1 (br.s., -NHAc), 1H, 5.8 (d., J=4.64, 3-H), 1H, 5.6 (dt-t. like, J=15.38, 6.47, 7-H), 1H, 5.4 (dt-t. like, J=15.38, 6.59, 6-H), 1H, 4.7 (ddd., J=7.56, 5.37, 4.64), 2H, 4.5 (s., 21-H$_2$), 1H, 3.6 (m, 14-H), 1H, 2.5 (ddd.,, J=14.77, 7.56, 6.59, 5-H), 1H, 2.4 (ddd., J=14.77, 6.59, 5.37, 5-H), 3H, 2.10 (s., Ac), 3H, 2.05 (s., Ac), 3H, 2.03 (s., Ac), 2H, 1.99

(m, 8-H), 20H, 1.3 (m, 9-13, 15-19-H), 3H, 0.9 (t., J=6.42).

EI-MS m/z: 511, 493, 426, 366, 332, 263, 129, 43.

(2)

Compound (5-i)

↓

AcOCH$_2$  OAc
AcNH——┬——
    O═C  O——(CH$_2$)$_6$CH(CH$_2$)$_5$CH$_3$
                    |
                    O—C—N⟋⟍N
                       ‖   ⟍⟋
                       S (5-ii)

The Compound (5-i) (386.6 mg) was dissolved in 2.1 ml of dry 1,2-dichloroethane, to which 273.7 mg of 1,1'-thiocarbonyldiimidazole was added. The solution was heated in an oil bath at 70° C. for 2 hours, and then cooled in water bath with ice for 10 minutes. To the yellow clear reaction mixture was added 20 ml of 1,2-dichloroethane, and the solution was washed with 10 ml of water, 10 ml of 1N hydrochloric acid (2 times), 10 ml of 5% sodium bicarbonate and 10 ml of water in order and the 1,2-dichloroethane layer was dried over magnesium sulfate. The residue (451.9 mg) obtained by concentration under reduced pressure was purified by chromatography on silica gel (18 g) column, eluted with a solution of chloroform:methanol=98:2, and further purified by thin-layer chromatography (eluent chloroform:methanol=9:1). The fractions of Rf 0.6 were collected and concentrated under reduced pressure to give 265.7 mg of the desired Compound (5-ii) as colorless, transparent oil. The fractions before and after those containing the desired compound were purified by preparative thin-layer chromatography using a mixture of chloroform:methanol=95:5 as an eluent and 121.0 mg of the desired Compound (5-ii) was obtained from the band of Rf 0.4 as colorless, transparent oil.

UV$\lambda_{max}^{EtOH}$: 274 nm ($\epsilon$=12,800).

IR$\nu_{max}^{CHCl_3}$ (cm$^{-1}$): 2910, 1780, 1760, 1680, 1460, 1380, 1290, 1230, 1100, 1040, 970.

$^1$HNMR (200 MHz, in CDCl$_3$, Ref. TMS) δ: 1H, 8.4 (br.s., imidazole ring), 1H, 7.6 (br.s., imidazole ring), 1H, 7.0 (d., J=0.74, imidazole ring), 1H, 6.3 (br.s., -NHAc), 1H, 5.8 (d., J=4.64, 3-H), 1H, 5.62 (qui., J=5.94, 14-H), 1H, 5.56 (br.dt., J=15.38, 6.35, 7-H), 1H, 5.4 (dt. like, J=15.38, 6.66, 6-H), 1H, 4.7 (dt., J=8.06, 4.95, 4-H), 2H, 4.5 (s., 21-H$_2$), 2H, 2.4 (m., 5-H$_2$), 3H, 2.10 (s., Ac), 3H, 2.05 (s., Ac), 3H, 2.03 (s., Ac), 2H, 2.00 (m, 8-H$_2$), 4H, 1.55 (m., 13, 15-H$_2$), 16H, 1.31 (br.s., 9-12, 16-19-H$_2$), 3H, 0.88 (t., J=6.48, 20-H$_3$).

EI-MS m/z: 493, 433, 374, 332, 263, 141, 129, 43.

(3)

Compound (5-ii)

↓

AcOCH$_2$  OAc
AcNH——┬——
    O═C  O——(CH$_2$)$_6$CH$_2$(CH$_2$)$_5$CH$_3$ (5-iii)

The Compound (5-ii) (60.0 mg) was dissolved in 4.5 ml of dry benzene, to which 41 μl of tributyltin hydride and then 5.0 mg of 2,2'-azo(isobutylonitrile) were added, and refluxed overnight. The yellow oily residue obtained by concentration under reduced pressure was partitioned between n-hexane and acetonitrile, and the acetonitrile layer was concentrated under reduced pressure. The residue (58.6 mg) was purified by preparative thin-layer chromatography (eluent: diethyl ether:n-hexane=9:1, developed 2 times), and 21.2 mg of the desired Compound (5-iii) was obtained from the band of Rf 0.4 as colorless, transparent oil.

[α]$_D$= +63.8° (c=0.994, CHCl$_3$).

IR$\nu_{max}^{CHCl_3}$ (cm$^{-1}$): 2910, 2840, 1780, 1755, 1685, 1500, 1370, 1220, 1036

$^1$HNMR (200 MHz, in CDCl$_3$, Ref. TMS) δ: 1H, 6.0 (br.s., -NHAc), 1H, 5.8 (d., J=4.39, 3-H), 1H, 5.6 (dt-t. like, J=15.26, 6.59, 7-H), 1H, 5.4 (dt-t. like, J=15.26, 7.08, 6-H), 1H, 4.7 (ddd., J=7.08, 5.62, 4.40, 4-H), 2H, 4.5 (br.s., 21-H$_2$), 2H, 2.4 (m., 5-H$_2$), 3H, 2.10 (s., Ac), 3H, 2.05 (s., Ac), 3H, 2.03 (s., Ac), 2H, 2.01 (m, 8-H$_2$), 22H, 1.3 (br.s., 9-19-H$_2$), 3H, 0.9 (t., J=6.35, 20-H$_3$).

EI-MS m/z: 495, 436, 376, 334, 265, 151, 129, 43.

(4) Synthesis of Compound (e) from Compound (5-iii)

The Compound (5-iii) (40.4 mg) was dissolved in 2 ml of methanol, to which 0.50 ml of 1N sodium hydroxide was added, and refluxed overnight under a nitrogen atmosphere. The solution was neutralized with 1N hydrochloric acid, and the precipitated white substance was filtered with suction and washed with water. Meanwhile, the filtrate was concentrated under reduced pressure to dryness, and water was added thereto. The insoluble substance was filtered with suction, washed with water, and recrystallized from methanol. Both insoluble substances were combined to give 19.4 mg of Compound (e) as white powder, m.p. 186° C.

[α]$_D$= +3.2° [c=1.00, MeOH-0.2N NaOH (1:1)].

IR$\nu_{max}^{KBr}$ (cm$^{-1}$): 3400, 3200, 3100, 2900, 1660, 1605, 1565, 1525, 1465, 1405, 1360, 1260, 1200, 1100, 1070, 1030, 960, 720.

$^1$HNMR (200 MHz, in CD$_3$OD, Ref. TMS) δ: 1H, 5.5 (dt-t. like, J=15.38, 5.86, 7-H), 1H, 5.4 (dt-t. like, J=15.38, 6.10, 6-H), 1H, 4.0 (d., J=10.98, 21-H), 1H, 3.9 (d., J=10.99, 21-H), 1H, 3.83 (br.t., J=7.33, 4-H), 1H, 3.78 (br.s., 3-H), 2H, 2.3 (br.t., J=6.84, 5-H$_2$), 2H, 2.0 (m, 8-H$_2$), 22H, 1.3 (br.s., 9-19-H$_2$), 3H, 0.9 (t., J=6.47, 20-H).

FAB-MS m/z: 388, 104, 57, 45, 29.

The physical properties of the sodium salt of Compound (e) are as follows:

m.p. 182°-185° C.

IR$\nu_{max}^{KBr}$ (cm$^{-1}$): 3400, 2900, 2850, 1580, 1470, 1405, 1040, 970, 720.

$^1$HNMR (400 MHz, in CD$_3$OD, Ref. TMS) δ: 2H, 5.5 (m, 6-H, 7-H), 1H, 3.8 (br.t., J=6.4, 4-H), 1H, 3.75 (br.s., 3-H), 1H, 3.7 (d., J=10.6, 21-H), 2H, 2.3 (br., 5-H$_2$), 2H, 2.0 (m., 8-H$_2$), 22H, 1.3 (br.s., 9-19H$_2$), 3H, 0.9 (t., J=6.47, 20-H).

Retention Time (HPLC): 19.5 minutes.

Measurement condition:

Column: YMC packed column AQ-312 (ODS) ϕ6 mm×150 mm.

Eluent: CH$_3$CN-0.05M HClO$_4$ buffer (pH 2.5) (6:4).

Flow speed: 1 ml/min.

Column temperature: 40° C.

Compound (e) is also synthesized as follows:

To the solution of 7.804 g of Compound (2-i) in anhydrous acetic acid (156 ml) saturated with hydrogen chloride was added about 29.5 g of activated zinc powder little by little with stirring slowly. After addition, stirring under cooling was continued for further 1.5 hours. The reaction mixture was filtered through cotton wool, poured into ice water, and the zinc powder residue was washed with ethyl acetate. The reaction mixture was extracted with the ethyl acetate layer which was used for washing, and the water layer was again extracted with ethyl acetate. The combined ethyl acetate layer was washed with aqueous solutions of saturated sodium bicarbonate and saturated sodium chloride in order, dried over magnesium sulfate, and concentrated under reduced pressure to give about 7 g of pale yellow oily residue. The thus-obtained residue was immediately purified by chromatography on silica gel (140 g) column (eluent: ethyl acetate:hexane=7:3) to give 6.204 g of a deoxo-compound represented by the following formula as colorless, transparent oil (yield 81.7%).

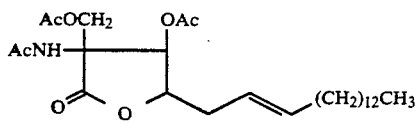
$(CH_2)_{12}CH_3$

IR$\nu_{max}$(CHCl$_3$) (cm$^{-1}$): 1780, 1755, 1685, 1500, 1030

$^1$HNMR (200 MHz, in CDCl$_3$, Ref:TMS) δ: 5.99 (1H, br.s., -NH), 5.79 (1H, d, J=4.4 Hz, 3-H), 5.58 (1H, dt.t-like, J=15.3, 6.6 Hz, 7-H), 5.39 (1H, dt.t-like, J=15.3, 7.1 Hz, 6-H), 4.71 (1H, ddd, J=7.1, 5.6, 4.4 Hz, 4-H), 4.52 (2H, br.s., 21-H$_2$), 2.39 (2H, m, 5-H$_2$), 2.10 (3H, s, -Ac), 2.05 (3H, s, -Ac), 2.03 (3H, s, -Ac), 2.01 (2H, m, 8-H$_2$), 1.26 (22H, br.s., 9-19-H$_2$), 0.88 (3H, t, J=6.4 Hz, 20-H$_3$).

$^{13}$C-NMR (50 MHz, in CDCl$_3$, Ref:TMS) δ: 172.44 (s, >C=O), 170.17 (s, >C=O), 169.42 (s, >C=O), 168.89 (s, >C=O), 135.29 (d, 6-C), 122.96 (d, 7-C), 81.66 (d, 4-C), 71.93 (d, 3-C), 62.73 (t, 21-C), 62.64 (s, 2-C), 32.57, 32.18, 31,91 (each t, 5-, 8-, 18-C), 29.68, 29.68, 29.68, 29.68, 29.68, 29.51, 29.36, 29.21, 29.21 (each t, 9-17-C), 22.77 (q, -COMe), 22.70 (t, 19-C), 20.58 (q, -COMe), 20.34 (q, -COMe), 14.11 (q, 20-C).

EI-MS m/z: 495, 436, 376, 334, 265, 151, 129, 43.

HREI-MS: C$_{27}$H$_{45}$NO$_7$ Calculated: 495.31975 Measured: 495.31864.

The deoxo-compound (3.102 g) described above was dissolved in 150 ml of methanol, to which 37.6 ml of 1N sodium hydroxide was added, and refluxed under heating overnight under a nitrogen atmosphere. The reaction mixture was neutralized with 1N hydrochloric acid, and the precipitated colorless substance was filtered with suction. The obtained precipitation was washed thoroughly with water and then washed once with a mixture of methanol-water (1:1), and dried under reduced pressure to give 2.018 g of Compound (e) (yield 83.2%), m.p. 186° C.

EXAMPLE 6

Synthesis of Compound (f)

(1)

Compound (2-i)

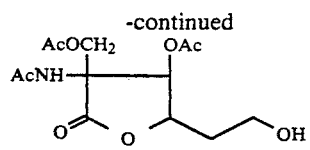

The Compound (2-i) (351.3 mg) was dissolved in 25 ml of dichloromethane, through which ozone was allowed to flow at −60° C. for 6 minutes. Oxygen was blown thereto to remove excess amount of ozone, and the reaction mixture was concentrated under reduced pressure in a water bath at room temperature. The obtained colorless, transparent oily residue was dissolved in 21.2 ml of dioxane, to which 8 ml of water was added. Several small pieces of dry ice were added thereto with stirring at room temperature. With disappearance of solid, 80.0 mg of sodium borohydride was added thereto. Thirty minutes later, the reaction mixture was acidified with 1N hydrochloric acid (not more than pH 2), and 10 minutes thereafter, the solution was adjusted to weak-acidic or neutral with 1N sodium hydroxide. The mixture was concentrated under reduced pressure to dryness in a water bath at 50° C. After completely removing moisture by an aspirator, chloroform (about 10 ml) was added to the solid residue which was partly white. The solution was heated and the insoluble substance was filtered off with suction. The residue (about 350 mg) which was obtained by concentration of the filtrate under reduced pressure was subjected to preparative thinlayer chromatography using a mixture of chloroform:methanol=9:1 as an eluent, and 106.0 mg of the desired Compound (6) was obtained from the band of Rf 0.3 as white foamy substance.

IR$\nu_{max}$CHCl$_3$ (cm$^{-1}$): 3400, 3000, 2900, 1780, 1755, 1680, 1500, 1370, 1225, 1050.

$^1$HNMR (200 MHz, in CDCl$_3$, Ref. TMS) δ: 1H, 6.3 (br.s., -NHAc), 1H, 5.8 (d., J=4.64, 3-H), 1H, 5.1 (ddd, J=9.03, 4.64, 4.39, 4-H), 2H, 4.5 (br.s., 7-H$_2$), 3H, 2.11 (s., Ac), 3H, 2.07 (s., Ac), 3H, 2.0 (s., Ac), 4H, 2.1–1.8 (m, 5, 6-H$_2$).

EI-MS m/z: 317, 274, 185, 167, 43

(2) Synthesis of Compound (f) from Compound (6)

The Compound (6) (70.0 mg) was dissolved in 1.33 ml of methanol, to which 3.99 ml of water and then 1.33 ml of 1N sodium hydroxide were added, and refluxed in an oil bath at 105° C. under a nitrogen atmosphere overnight. After cooling, the solution was charged in the column which had been packed with 6 ml of IRC-50 (H$^+$ type) and eluted with water-methanol (8:2). The eluate (30 ml) was concentrated under reduced pressure in a water bath at 50° C., and the resultant yellow-brown residue was sucked in an desiccator over sodium hydroxide to remove acetic acid. Thereto was added water (a little less than 2 ml), and a small amount of the precipitated insoluble substance was filtered off. The filtrate was concentrated under reduced pressure, to which water was added to a total amount of a little less than 2 ml. To this solution was added methanol at room temperature until the solution became slightly turbid and the solution was kept standing for 3 hours to give 14.0 mg of Compound (f) as colorless, transparent scales, m.p. 209.5°–219.0° C. (decomposition).

$^1$HNMR (200 MHz, in D$_2$O, Ref. DSS) δ: 1H, 4.03 (d., J=11.72, 7H), 1H, 3.95 (ddd., J=8.30, 5.12, 1.22, 4-H), 1H, 3.9 (d., J=11.72, 7-H), 1H, 3.8 (d., J=1.2, 3-H), 2H, 3.7 (br.dd., J=7.08, 6.35, 6-H$_2$), 1H, 1.87

(ddt., J=14.16, 8.30, 6.10, 5-H), 1H, 1.74 (dtd., J=14.16, 7.08, 5.12, 5-H).

The present invention has been appropriately and sufficiently in the foregoing specification including Examples, which can be changed or modified within the spirit and scope of the invention.

What is claimed is:

1. A 2-aminopentanoic acid compound represented by the formula

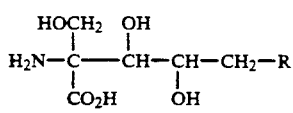  (I)

wherein R is a straight or branched chain alkyl of 1 to 30 carbon atoms, a hydroxyalkyl wherein the alkyl moiety has 1 to 6 carbon atoms or a group represented by the formula: —CH=CH(CH$_2$)$_n$CH=CH—CH(OH)—(CH$_2$)$_m$CH$_3$ wherein n and m stand for an integer of 1 to 10, respectively; —CH=CH(CH$_2$)$_p$—C(=X)—(CH$_2$)$_q$CH$_3$ wherein >C=X stands for

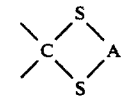

wherein A is an alkylene of 1 to 4 carbon atoms, >C=N—OB wherein B is a hydrogen or a straight or branched alkyl of 1 to 4 carbon atoms, or >CHNH$_2$ wherein p and q are respectively an integer of 1 to 10; or —CH=CH—Y wherein Y is a straight or branched alkyl of 1 to 30 carbon atoms, a salt thereof, a γ-lactone compound thereof having the formula

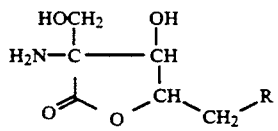

wherein R is as defined above and a compound protected by an amino or hydroxy-protecting group.

2. The compound as claimed in claim 1, selected from among the following compounds (a) to (f):

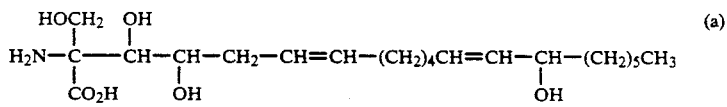  (a)

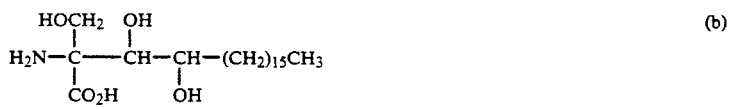  (b)

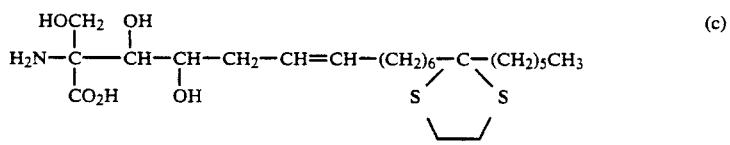  (c)

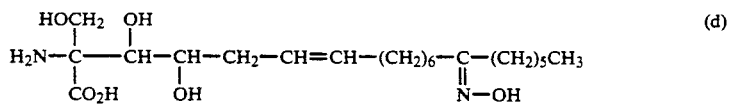  (d)

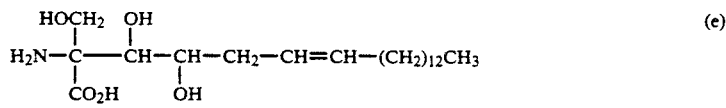  (e)

  (f)

an optical isomer thereof or a pharmacologically acceptable salt thereof.

3. An immunosuppressant comprising a compound as claimed in claim 1.

4. An immunosuppressants comprising a compound as claimed in claim 2.

* * * * *